(12) United States Patent
Kanno et al.

(10) Patent No.: US 7,557,152 B2
(45) Date of Patent: Jul. 7, 2009

(54) REACTIVE FLAME RETARDANT AND FLAME-RETARDANT RESIN PROCESSED ARTICLE

(75) Inventors: Toshiyuki Kanno, Hino (JP); Yoshinobu Sugata, Hino (JP); Hironori Yanase, Hino (JP); Kiyotaka Shigehara, Fuchu (JP)

(73) Assignee: Fuji Electric Holdings Co., Ltd., Kawasaki-shi (JP)

( * ) Notice: Subject to any disclaimer, the term of this patent is extended or adjusted under 35 U.S.C. 154(b) by 99 days.

(21) Appl. No.: 11/816,665

(22) PCT Filed: Feb. 16, 2006

(86) PCT No.: PCT/JP2006/302724

§ 371 (c)(1),
(2), (4) Date: Aug. 20, 2007

(87) PCT Pub. No.: WO2006/088086

PCT Pub. Date: Aug. 24, 2006

(65) Prior Publication Data

US 2009/0043032 A1 Feb. 12, 2009

(30) Foreign Application Priority Data

Feb. 21, 2005 (JP) .............................. 2005-043855
Feb. 21, 2005 (JP) .............................. 2005-043865

(51) Int. Cl.
*C08K 5/53* (2006.01)
*C08K 5/161* (2006.01)
(52) U.S. Cl. ...................................................... 524/126
(58) Field of Classification Search ................. 524/126
See application file for complete search history.

(56) References Cited

U.S. PATENT DOCUMENTS 6,774,163 B2 * 8/2004 Janke et al. ................. 524/127

FOREIGN PATENT DOCUMENTS

| JP | 55 770 | 1/1980 |
|----|--------|--------|
| JP | 5 331179 | 12/1993 |
| JP | 8 193090 | 7/1996 |
| JP | 2002 20394 | 1/2002 |
| JP | 2002 80633 | 3/2002 |
| JP | 2002 138096 | 5/2002 |
| JP | 2003 327795 | 11/2003 |
| JP | 2004 250539 | 9/2004 |
| JP | 2004 315672 | 11/2004 |
| WO | 2005 012415 | 2/2005 |

* cited by examiner

*Primary Examiner*—Ling-Siu Choi
*Assistant Examiner*—Hui Chin
(74) *Attorney, Agent, or Firm*—Oblon, Spivak, McClelland, Maier & Neustadt, P.C.

(57) ABSTRACT

Disclosed is a reactive flame retardant which provides a resin with excellent flame retardance even when it is added in a small amount while being prevented from bleedout. Also disclosed is a flame-retardant resin processed article obtained by using such a reactive flame retardant. An organophosphorus compound represented by the general formula (I) below, wherein at least one or more of $X^1$-$X^3$ represent a group containing phosphorus and having a terminal unsaturated group, is used as a reactive flame retardant which is reactive with resins. A flame-retardant resin processed article can be obtained by solidifying the resin composition containing the organophosphorus compound and then reacting it through heating or application of radiation.

13 Claims, 2 Drawing Sheets

[Figure 1]
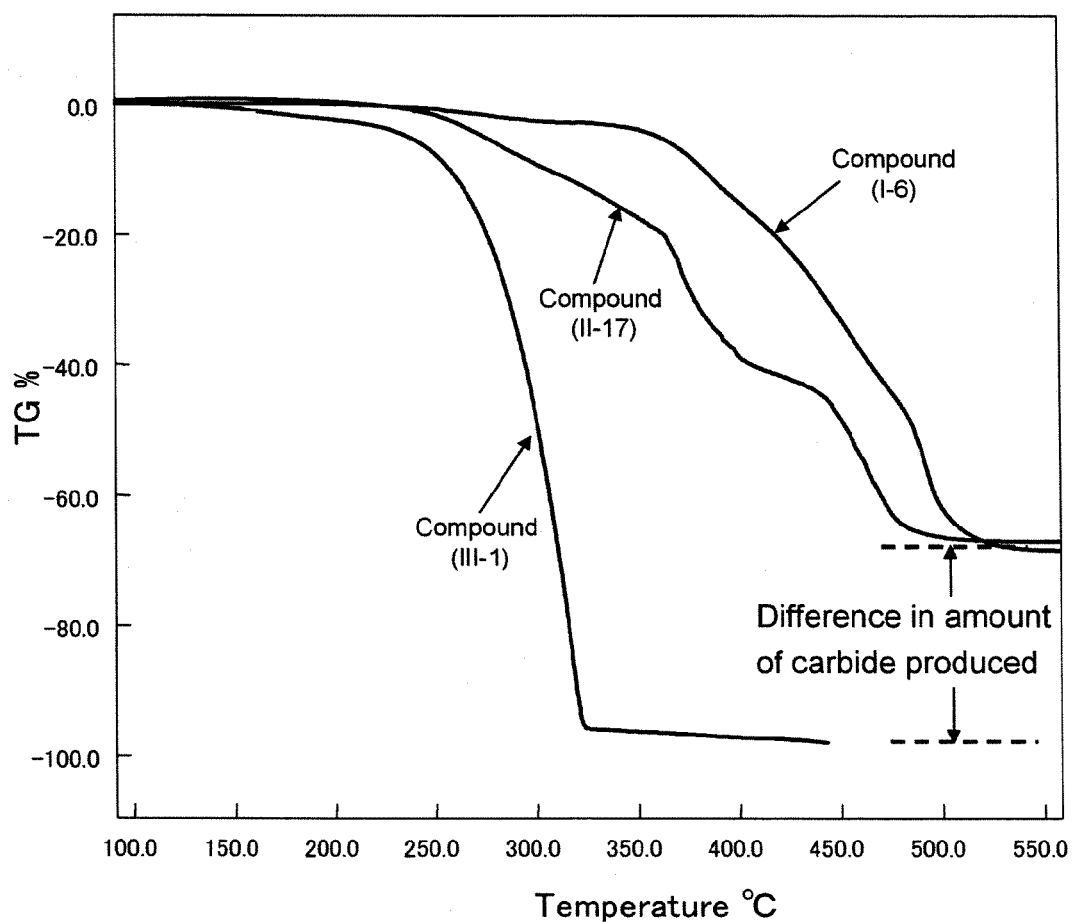

[Figure 2]
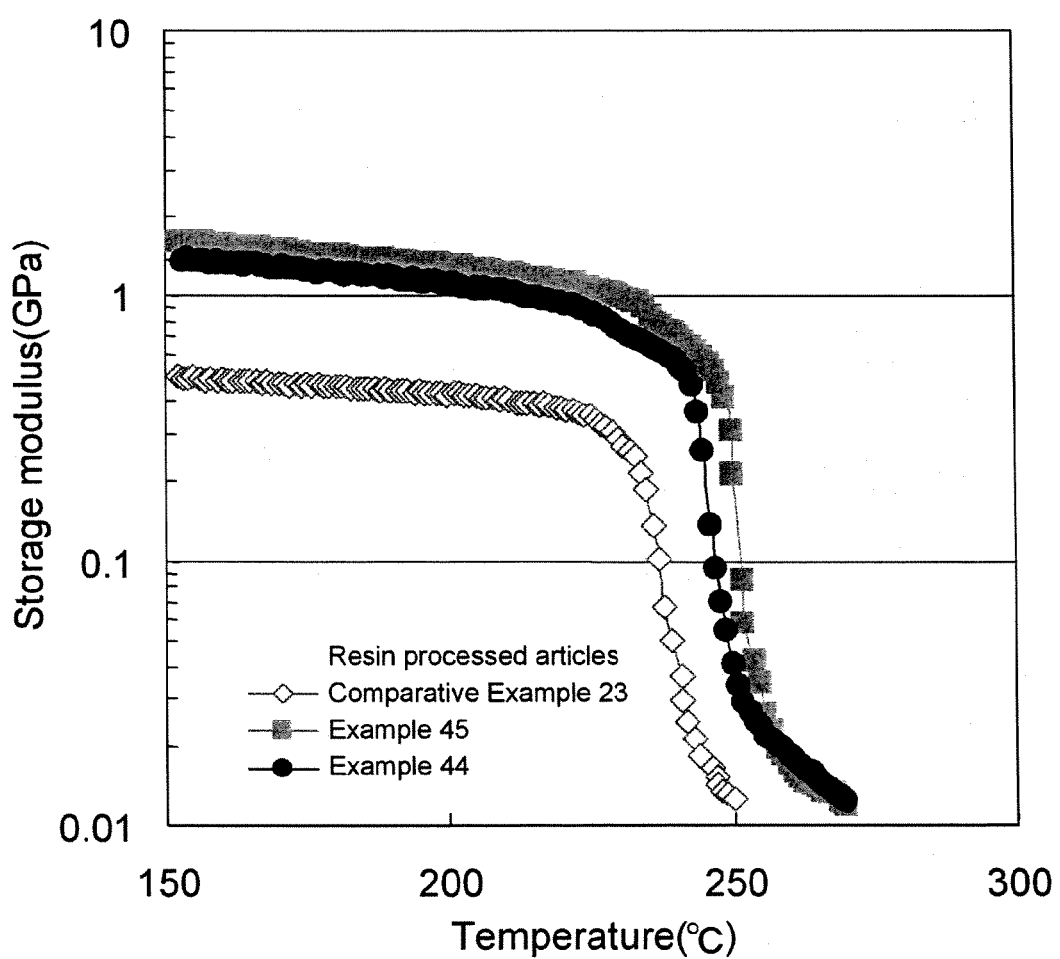

REACTIVE FLAME RETARDANT AND FLAME-RETARDANT RESIN PROCESSED ARTICLE

TECHNICAL FIELD

The present invention relates to a flame retardant for use in a resin molded article or the like and a flame-retardant resin processed article using the same. More specifically, the present invention relates to a non-halogen-based flame retardant containing no halogen and a flame-retardant resin processed article using the same.

BACKGROUND ART

Thermoplastic resins such as polyester and polyamide, and thermosetting resins such as epoxy each have excellent moldability or processability, mechanical strength, and electrical characteristics for a general-purpose resin and an engineering plastic, and thus have been used in various fields including the fields of electricity and electronics. In addition, resin processed articles obtained by processing and molding those resins are required to be flame retardant in terms of safety for the purpose of preventing a fire at a high temperature. For example, specifications such as UL94 have been provided as flame retardance grades.

It is generally known that a halogen substance is effective in making such a resin processed article or the like flame-retardant. Flame retardance is imparted to the resin processed article or the like by adding a halogen-based flame retardant to a resin. The mechanism via which flame retardance is imparted by the halogen-based flame retardant is said to be as follows. That is, a halogenated radical is produced mainly by heat decomposition, and the produced halogenated radical captures an organic radical being a combustion source to stop the chain reaction of combustion, whereby high flame retardance is expressed.

However, a flame retardant containing a large amount of halogen compound may generate dioxin and the like depending on combustion conditions, so there has been a growing demand for reducing the amount of halogen in recent years from the viewpoint of reducing a load to the environment. Therefore, various non-halogen-based flame retardants each containing no halogen-based compound have been examined.

Inorganic flame retardants such as a metal hydrate and red phosphorus, triazine-based flame retardants derived from carbamide, organophosphorus-based flame retardants such as a phosphoric acid ester, and the like have been examined as such non-halogen-based flame retardants.

However, a metal hydrate such as aluminum hydroxide or magnesium hydroxide does not have a very high flame retardance imparting effect, so the metal hydrate must be blended with a large amount of resin. Therefore, the moldability of a resin is apt to deteriorate and the mechanical strength of a molded article to be obtained or the like is apt to reduce, thereby causing a problem in that applications of a usable resin processed article or the like are limited. In addition, red phosphorus is apt to inhibit electrical characteristics owing to insufficient dispersion, generate a dangerous gas, reduce moldability, and cause bleeding, although it has a high flame retardance effect.

On the other hand, for example, Patent Document 1 below discloses that a piperazine salt or alkylenediamine salt having 1 to 6 carbon atoms of an acidic phosphoric acid ester that has a phosphorinane structure is used as a flame retardant being an organophosphorus-based flame retardant such as a phosphoric acid ester.

In addition, Patent Document 2 below discloses a flame retardant for a resin mainly composed of a salt composed of an aromatic phosphoric acid ester such as monophenyl phosphate or monotolyl phosphate and an aliphatic amine such as piperazine.

Further, Patent Document 3 below discloses a phosphorus-containing phenol compound used as a flame retardant for providing a flame-retardant epoxy resin, which exerts an excellent flame retardance effect with a halogen-free flame-retardant prescription, providing a molded article excellent in physical properties such as heat resistance and water resistance and in adhesiveness in an electrical laminated plate application.

Further, Patent Document 4 below discloses an organic cyclic phosphorus compound having a bifunctional hydroxyl group particularly useful as a stabilizer for a polymer compound or as a flame retardant.

In addition, Patent Document 5 below discloses an organophosphorus compound having an allyl group as an unsaturated bond at a terminal of the compound.

Patent Document 1: JP 2002-20394 A
Patent Document 2: JP 2002-80633 A
Patent Document 3: JP 2002-138096 A
Patent Document 4: JP 5-331179 A
Patent Document 5: JP 2004-315672 A

DISCLOSURE OF THE INVENTION

Problems to be Solved by the Invention

As disclosed in Patent Documents 1 to 5 above, various investigations have been conducted on a flame retardant composed of an organophosphorus compound, and various organophosphorus flame retardants are currently available. However, each of those organophosphorus flame retardants has insufficient flame retardance, so a resin must be blended with a high concentration of each of the flame retardants.

In addition, none of the organophosphorus-based compounds disclosed in Patent Documents 1 to 3 above has a reactive group for reacting with a resin component in a molecule, so a flame retardant component is apt to migrate in a resin, thereby causing a problem in that the flame retardant component volatilizes at the time of molding to contaminate a die or a flame retardant bleeds out to the surface of the resin processed article.

An organophosphorus-based compound described in Patent Document 4 above functions as a reactive flame retardant in a resin having a reactive group capable of binding to a hydroxyl group like in an epoxy resin. However, crosslinkage cannot be formed in a resin having no reactive group capable of binding to a hydroxyl group like in a typical olefin resin. In this case as well, a flame retardant component is apt to migrate in a resin, thereby causing a problem in that the flame retardant component volatilizes at the time of molding to contaminate a die or a flame retardant bleeds out to the surface of the resin processed article.

In addition, the organophosphorus compound disclosed in Patent Document 5 above is reactive with a resin, and functions as a reactive flame retardant. However, the compound is a liquid at room temperature, so the presence of a product that has not reacted with the resin is apt to cause the bleedout of the compound. In addition, the organophosphorus compound has a low heat decomposition temperature, and its flame retardant component is apt to vaporize upon kneading and molding with the resin. Accordingly, in some cases, the flame retardant cannot be contained in a molded article with sufficient amount, so that it cannot exert flame-retarding effect. Therefore, the molded article with the organophosphorus compound has poor moldability or pocessability.

Therefore, it is an object of the present invention to provide: a reactive flame retardant which has excellent flame retardance and heat resistance even when added to a resin in a small amount, which can be prevented from bleedout or the like, and which has excellent mechanical characteristics, electrical characteristics, dimensional stability, and moldability of a molded article; and a flame-retardant resin processed article using the same.

Means for Solving the Problems

The inventors of the present invention have made extensive studies with a view to solving the above-mentioned problems. A reactive flame retardant of the present invention as a result of the studies is characterized by containing an organophosphorus compound represented by the following general formula (I) or (II), the organophosphorus compound having a terminal unsaturated group:

[Chem 1]

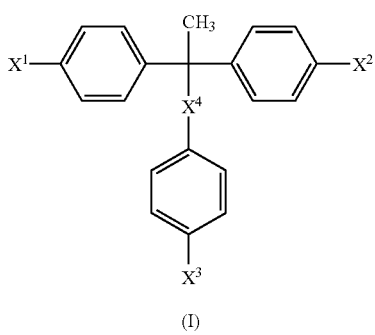

(I)

where $X^1$ to $X^3$ each independently represent —OH or a group represented by the following formula (A), $X^4$ represents a single bond or a group represented by the following formula (B), and one or more of $X^1$ to $X^3$ each represent a group represented by the following formula (A) and containing $CH_2\!=\!CH\!-\!CH_2\!-$ at a terminal of the group;

[Chem 2]

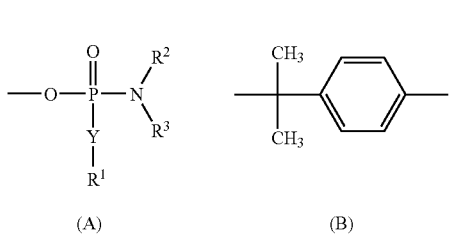

(A)  (B)

where $R^1$ represents $CH_2\!=\!CH\!-\!CH_2\!-$, an aryl group having 12 or less carbon atoms, or an aralkyl group having 12 or less carbon atoms, $R^2$ and $R^3$ each independently represent a hydrogen atom, $CH_2\!=\!CH\!-\!CH_2\!-$, an aryl group having 12 or less carbon atoms, or an aralkyl group having 12 or less carbon atoms, and Y represents a single bond, —NH—, or —O—;

[Chem 3]

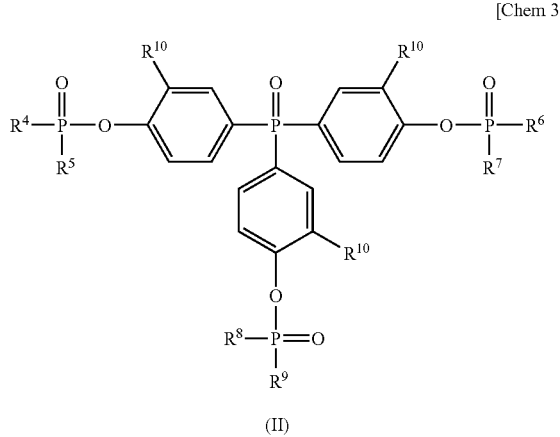

(II)

where $R^4$ to $R^9$ each represent a group selected from phenyl, benzyl, α-naphthyl, β-naphthyl, p-biphenyl, phenoxy, benzyloxy, α-naphthoxy, β-naphthoxy, p-biphenyloxy, $(CH_2\!=\!CH\!-\!CH_2)_2N\!-$, $CH_2\!=\!CH\!-\!CH_2NH\!-$, $CH_2\!=\!CH\!-\!CH_2O\!-$, and $CH_2\!=\!CH\!-\!CH_2\!-$ groups, $R^{10}$ represents H or $CH_2\!=\!CH\!-\!CH_2\!-$, at least one of $R^4$ to $R^{10}$ represents a group containing $CH_2\!=\!CH\!-\!CH_2\!-$ at a terminal of the group, and $R^4$ to $R^9$ may be identical to or different from one another.

According to the reactive flame retardant of the present invention, an organophosphorus compound having at least one end unsaturated bond in one molecule is used, so the end unsaturated bond can be bound to a resin due to heat or a radiation for a reaction. Thus, a flame retardant component can be stably present in the resin, so the flame retardant can be prevented from bleedout and flame retardance can be imparted for a long time period even when the flame retardant is added in a small amount.

In addition, the organophosphorus compound of the present invention contains one or more phosphorus atoms in any one of its molecules, so the compound can easily produce a P radical having a high flame-retarding effect. Further, when the compound contains a P—C bond that can easily dissociate, the compound is more likely to produce a P radical having a high flame-retarding effect. Therefore, flame retardance can be improved.

In addition, the heat decomposition temperature of the organophosphorus compound can be increased because the compound has a high molecular weight, and is energetically stable. Accordingly, the compound can prevent the vaporization of a flame retardant at the time of kneading and molding with a resin, and can prevent the decomposition of the flame retardant due to heat or shearing at the time of the molding, whereby the moldability with the compound is improved. Further, the compound contains a large amount of carbon, whereby the so-called char effect in which flame retardance is improved by the production and deposition of a soot component at the time of the decomposition of the resin can be obtained.

Meanwhile, the flame-retardant resin processed article of the present invention is obtained by molding or applying a resin composition containing the reactive flame retardant and a resin and then reacting the resin by heating or irradiation with a radiation with the reactive flame retardant, in which the flame-retardant resin processed article is characterized by containing 1 to 20 mass % of the reactive flame retardant with respect to the entirety of the flame-retardant resin processed article.

According to the flame-retardant resin processed article of the present invention, since the unsaturated bond at the end of the organophosphorus compound is caused to react with the resin by heating or irradiation with a radiation, a flame retardant component is stably present in the resin. As a result, the flame retardant can be prevented from bleedout and a flame retardance effect can be improved. Therefore, flame retardance can be imparted for a long time period even when the amount of the reactive flame retardant to be added to the entirety of the flame-retardant resin processed article is as small as 1 to 20 mass %.

In addition, through bonding between the flame retardant and the resin, the resin crosslinks to provide a three-dimensional network structure. Therefore, a resin molded article can be obtained, with which the resin processed product obtained can be excellent in all of chemical stability, heat resistance, mechanical characteristics, electrical characteristics, dimensional stability, flame retardance, and moldability.

In particular, heat resistance and mechanical strength can be improved. Further, the resin can be molded into a thin shape.

In the above-mentioned flame-retardant resin processed article, the resin composition preferably contains two or more kinds of the reactive flame retardants at least one kind of which is multifunctional.

According to this aspect, since the reaction rate accompanied by crosslinking can be in control through combinational use of flame retardants different from each other in reactivity, the contraction, and the like of the resin due to the abrupt advancement of a crosslinking reaction can be prevented. In addition, the incorporation of a multifunctional flame retardant results in the formation of a uniform three-dimensional network structure with the organophosphorus compound, so heat resistance and flame retardance are improved and more stable physical properties of resin are obtained.

In addition, in the above-mentioned flame-retardant resin processed article, the resin composition preferably further contains, other than the reactive flame retardant, a flame retardant being a cyclic nitrogen-containing compound having at least one unsaturated group at a terminal of the compound.

According to this aspect, with the cyclic nitrogen-containing compound having at least one unsaturated group at the end thereof, through bonding between the flame retardant and the resin, the resin crosslinks to provide a three-dimensional network structure as well. Therefore, while the entire cost of the flame retardants can be reduced owing to the combined use of the flame retardants, a resin molded article can be obtained, with which the resin processed product obtained can be excellent in all of chemical stability, heat resistance, mechanical characteristics, electrical characteristics, dimensional stability, flame retardance, and moldability. In addition, the incorporation of nitrogen additionally improves compatibility with the resin particularly in the case where a polyamide-based resin is used as the resin.

In addition, in the above-mentioned flame-retardant resin processed article, the resin composition may further contain a flame retardant being an addition type flame retardant having no reactivity except the reactive flame retardant. The resin composition desirably contains the addition type flame retardant in a polymer matrix in combination with the reactive flame retardant to such an extent that the addition type flame retardant does not affect the thermal and mechanical characteristics of the resin processed article, and does not bleed.

According to this aspect, the combined use of the reactive flame retardant with an addition type flame retardant having no reactivity such as a phosphoric acid ester-based, melamine-based, metal hydroxide, or silicon-based flame retardant can additionally improve flame retardance owing to a synergistic effect as compared to that in the case where the reactive flame retardant is used alone, and can reduce the cost of the flame retardant.

Further, in the flame-retardant resin processed article, the resin composition preferably further contains a crosslinking agent which is a multifunctional monomer or oligomer having an unsaturated group at an end of its main skeleton thereof.

According to this aspect as well, through bonding between the flame retardant and the resin, the resin crosslinks to provide a three-dimensional network structure. Therefore, a resin molded article can be obtained, with which the resin processed product obtained can be excellent in all of chemical stability, heat resistance, mechanical characteristics, electrical characteristics, dimensional stability, flame retardance, and moldability.

Further, in the flame-retardant resin processed article, the flame-retardant resin processed article preferably further contains 1 to 45 mass % of an inorganic filler with respect to the entirety of the flame-retardant resin processed article. In particular, the flame-retardant resin processed article preferably contains 1 to 10 mass % of a laminar clay obtained by laminating silicate layers as the inorganic filler with respect to the entirety of the flame-retardant resin processed article. According to this aspect, a resin processed article, the contraction and decomposition thereof due to crosslinking being suppressed, which is excellent in dimensional stability, can be obtained. In addition, when laminar clay obtained by laminating silicate layers is incorporated as the inorganic filler, the laminar clay is dispersed into the resin in a nano order to form a hybrid structure with the resin. This leads to an improvement in the heat resistance, mechanical strength, and the like of the flame-retardant resin processed article to be obtained.

Further, in the flame-retardant resin processed article, the flame-retardant resin processed article preferably further contains 5 to 50 mass % of reinforced fibers with respect to the entirety of the flame-retardant resin processed article. According to this aspect, the incorporation of the reinforced fibers can improve the mechanical strength of the resin processed article such as tensile strength, compressive strength, bending strength, or impact strength. Further, reductions in physical properties due to moisture and temperature can be prevented.

Further, in the flame-retardant resin processed article, the flame-retardant resin processed article is preferably obtained by a reaction between the resin and the reactive flame retardant through irradiation with an electron beam or γ ray at a dose of 10 kGy or more. According to this aspect, after having been solidified by molding or the like, the resin can be crosslinked by a radiation, so a resin processed article can be produced with high productivity. In addition, at a dose in the above range, uneven formation of a three-dimensional network structure due to an insufficient dose can be prevented as well as bleedout due to the remaining of an unreacted crosslinking agent. In particular, at an irradiation dose of 10 to 45 kGy, deformation due to the internal strain of the resin processed article, contraction, and the like resulting from an oxidation decomposition product generated by an excessive dose, can be prevented as well.

Further, in the flame-retardant resin processed article, the flame-retardant resin processed article is also preferably obtained by a reaction between the resin and the reactive flame retardant at a temperature higher than the temperature at which the resin composition is molded by 5° C. or higher. According to this aspect, a radiation irradiator or the like is not needed. In particular the flame-retardant resin processed article can be suitably used for a resin composition containing a thermosetting resin.

In further aspect of the flame-retardant resin processed article, the flame-retardant resin processed article is preferably one selected from a molded article, a coating film, and a sealing compound. As described above, the flame-retardant resin processed article of the present invention has excellent flame retardance and can be prevented from bleedout. Therefore, in addition to the use as a typical resin molded article, it can be formed into a coating film as a coating agent or the like or can be suitably used as a sealing compound for a semiconductor, a liquid crystal material, or the like.

In further aspect of the flame-retardant resin processed article, the flame-retardant resin processed article is preferably used as an electrical component or an electronic component. As described above, the flame-retardant resin processed article of the present invention is excellent in all of heat resistance, mechanical characteristics, electrical characteristics, dimensional stability, flame retardancy, and moldability, so it can be particularly suitably used as an electrical component or an electronic component in which the above physical properties are particularly stringently demanded.

EFFECT OF THE INVENTION

According to the present invention, there can be provided: a non-halogen-based reactive flame retardant which provides a resin with excellent flame retardance even when it is added to the resin in a small amount while being prevented from bleedout or the like; and a flame-retardant resin processed article using the reactive flame retardant.

BRIEF DESCRIPTION OF THE DRAWINGS

FIG. 1 is a graph showing the TG curve of a flame retardant.

FIG. 2 is a graph showing a relationship between the temperature and mechanical strength of a flame-retardant resin processed article.

BEST MODE FOR CARRYING OUT THE INVENTION

Hereinafter, the present invention will be described in detail.

The reactive flame retardant of the present invention is a reactive flame retardant that has reactivity with a resin and binds with the resin due to the reactivity to impart flame retardance, and is characterized by containing a reactive organophosphorus compound represented by the following general formula (I) or (II):

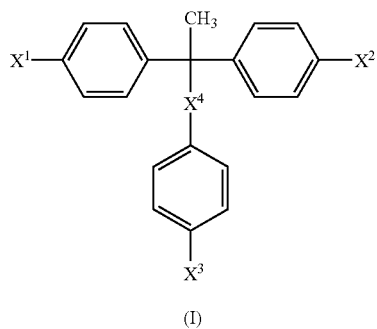

(I)

where $X^1$ to $X^3$ each independently represent —OH or a group represented by the following formula (A), $X^4$ represents a single bond or a group represented by the following formula (B), and one or more of $X^1$ to $X^3$ each represent a group represented by the following formula (A) and containing $CH_2=CH-CH_2-$ at a terminal of the group;

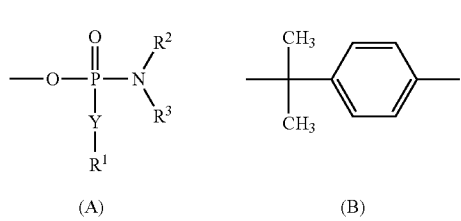

(A)   (B)

where $R^1$ represents $CH_2=CH-CH_2-$, an aryl group having 12 or less carbon atoms, or an aralkyl group having 12 or less carbon atoms, $R^2$ and $R^3$ each independently represent a hydrogen atom, $CH_2=CH-CH_2-$, an aryl group having 12 or less carbon atoms, or an aralkyl group having 12 or less carbon atoms, and Y represents a single bond, —NH—, or —O—;

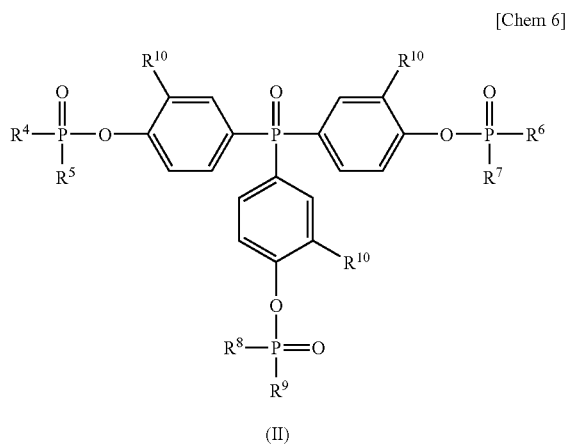

(II)

where $R^4$ to $R^9$ each represent a group selected from phenyl, benzyl, α-naphthyl, β-naphthyl, p-biphenyl, phenoxy, benzyloxy, α-naphthoxy, β-naphthoxy, p-biphenyloxy, $(CH_2=CH-CH_2)_2N-$, $CH_2=CH-CH_2NH-$, $CH_2=CH-CH_2O-$, and $CH_2=CH-CH_2-$ groups, $R^{10}$ represents H or $CH_2=CH-CH_2-$, at least one of $R^4$ to $R^{10}$ represents a group containing $CH_2=CH-CH_2-$ at a terminal of the group, and $R^4$ to $R^9$ may be identical to or different from one another.

The organophosphorus compound of the present invention represented by any one of the above-mentioned general formulae (I) and (II) is a compound in which phosphorus is pentavalent, and which has one or more allyl groups ($CH_2=CH-CH_2-$) each being an unsaturated bond at a terminal of the compound. Here, an allyl group is a functional group to be bonded to a resin through heating or the application of radiation or the like to be described later.

Because the above-mentioned organophosphorus compound of the present invention has powdery characteristics at room temperature, the bleedout of the compound hardly occurs even when a product that has not reacted with a resin remains in a molded article. In addition, the organophosphorus compound of the present invention has a heat decomposition temperature higher than that of a conventional reactive organophosphorus compound, and is more energetically stable than the conventional reactive organophosphorus compound, so its flame retardant component hardly vaporizes upon molding, and a resin processed article has excellent moldability or pocessability. Further, the organophosphorus compound of the present invention contains a large number of aromatic rings in its molecules, so the carbide producing ratio is high, and a char (pyrolysis residue) exhibiting an extremely large shielding action on heat or oxygen can be easily formed. In addition, the organophosphorus compound of the present invention has a high phosphorus content, so a phosphorus radical having a high flame-retarding effect can be easily produced at the time of heat decomposition. In addition, the organophosphorus compound of the present invention has a steric molecular structure, so the compound is highly reactive with a resin, and can improve the mechanical strength of a resin molded article to be obtained. Even in the case of a resin molded article composed of a thermoplastic resin, the resin molded article can have mechanical physical properties comparable to those of a thermosetting resin.

The organophosphorus compound represented by the general formula (I) preferably has two or more allyl groups in any one of its molecules. In addition, the compound preferably has two or more phosphorus atoms in any one of its molecules. In addition, the phosphorus content of the compound is preferably 6 to 20 mass %.

In addition, examples of the aryl group having 12 or less carbon atoms in the general formula (I) include —C$_6$H$_5$ (phenyl group), —C$_6$H$_5$OH (hydroxyphenyl group), —C$_6$H$_5$—C$_6$H$_5$OH (hydroxybiphenyl group), -α-C$_{10}$H$_7$ (α-naphthyl group), and -β-C$_{10}$H$_7$ (β-naphthyl group).

In addition, an example of the aralkyl group having 12 or less carbon atoms is —CH$_2$—C$_6$H$_5$ (benzyl group)

In addition, Y in the formula (A) preferably represents a single bond. When Y represents a single bond, the compound has a P—C bond that can easily dissociate, so the compound can easily produce a phosphorus radical at the time of heat decomposition, and hence flame retardance can be further improved.

Specific examples of the organophosphorus compound represented by the general formula (I) include Compounds (I-1) to (I-6) shown below.

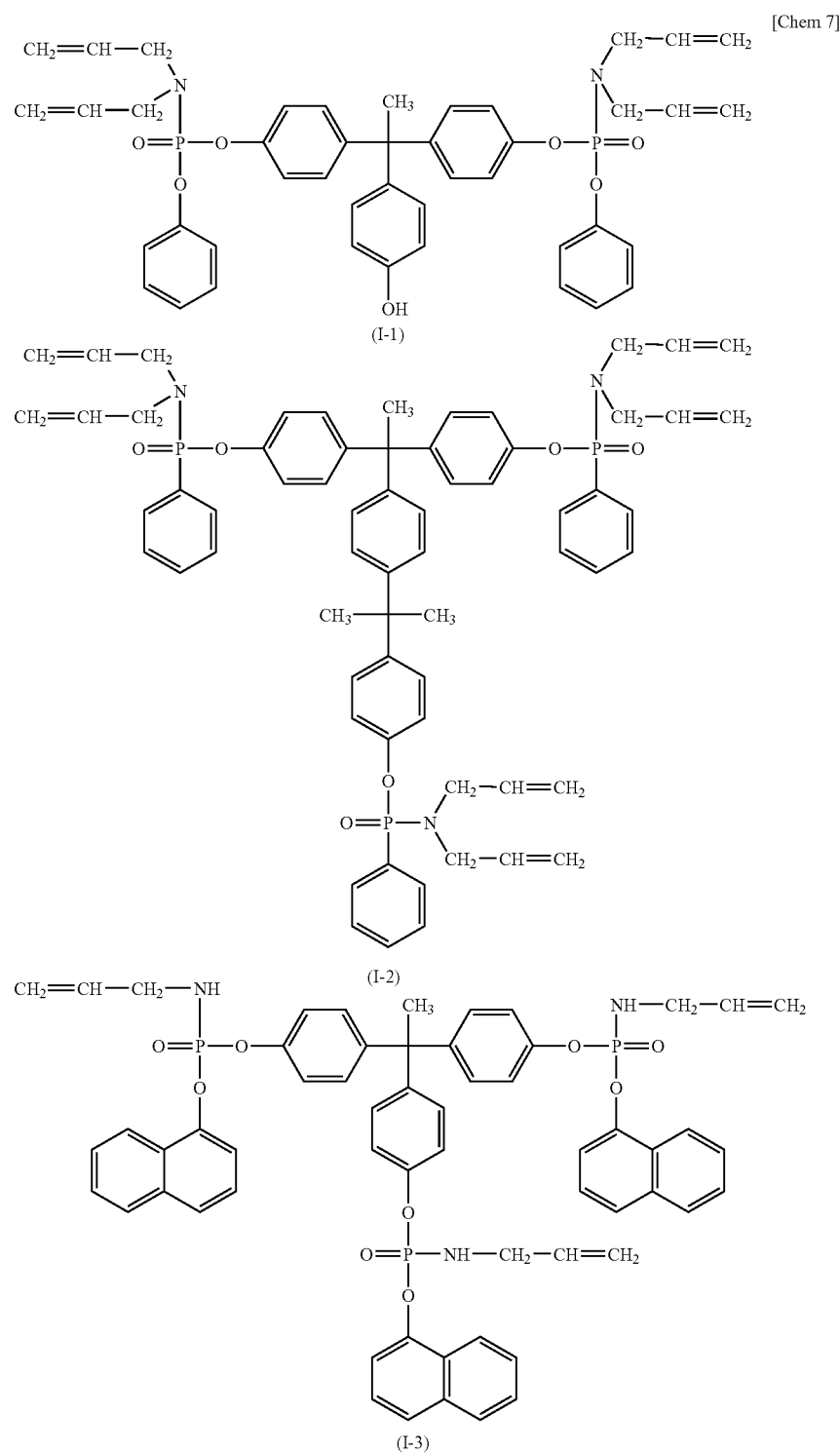

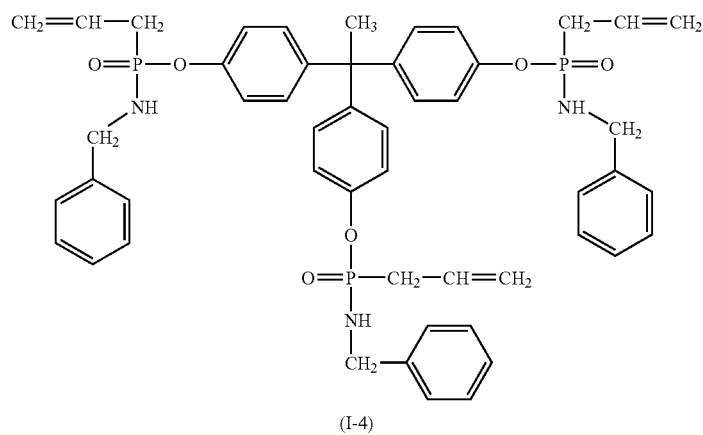
(I-4)
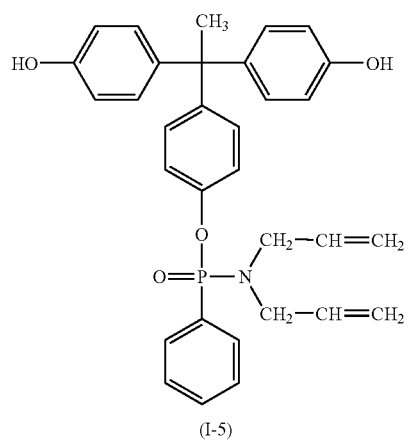
(I-5)
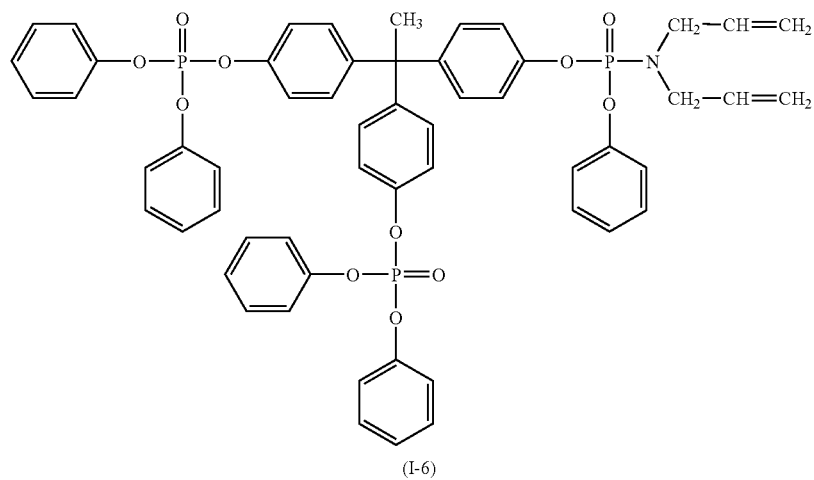
(I-6)

Each of those compounds can be synthesized by, for example, a reaction between a phenol resin having a structure represented by the following formula (d) or (e) and an acid chloride compound having a structure represented by the formula (A).

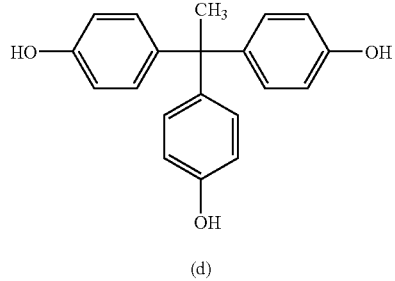

(d)

[Chem 9]

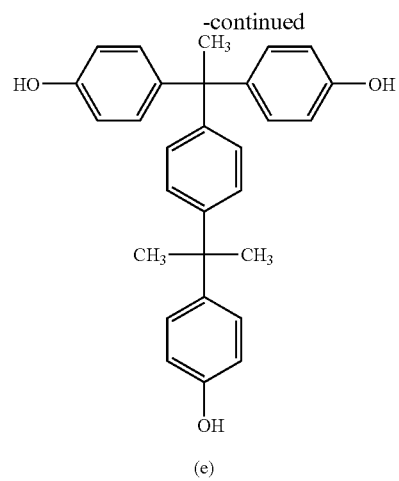

(e)

In addition, the organophosphorus compound represented by the general formula (II) preferably has two or more allyl groups in any one of its molecules. In addition, the phosphorus content of the compound is preferably 6 to 20 mass %.

In addition, specific examples of the organophosphorus compound represented by the general formula (II) include Compounds (II-1) to (II-17) shown below.

[Chem 10]

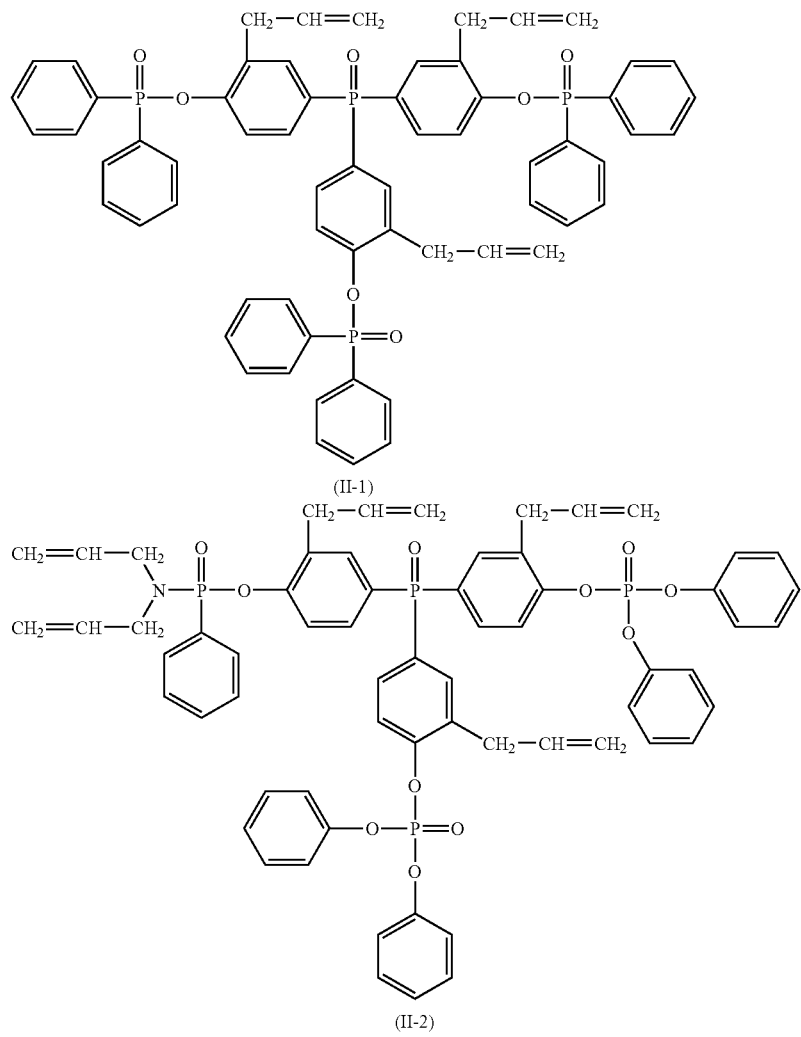

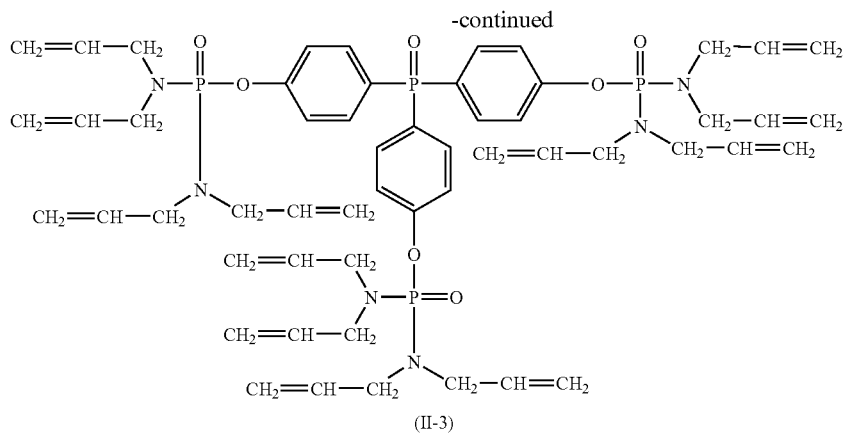
(II-3)
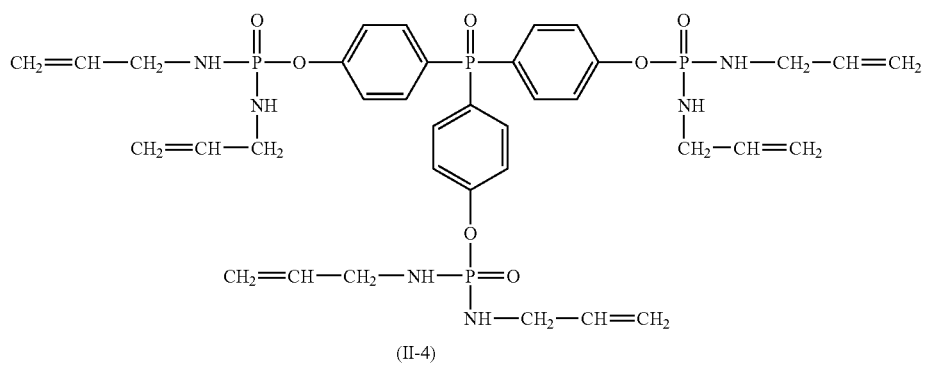
(II-4)
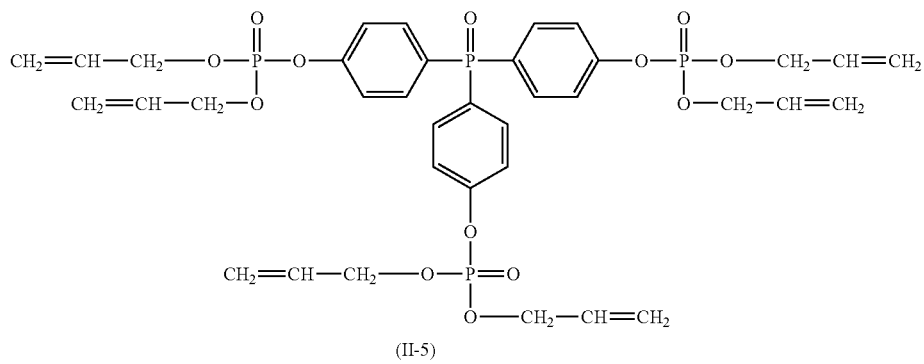
(II-5)
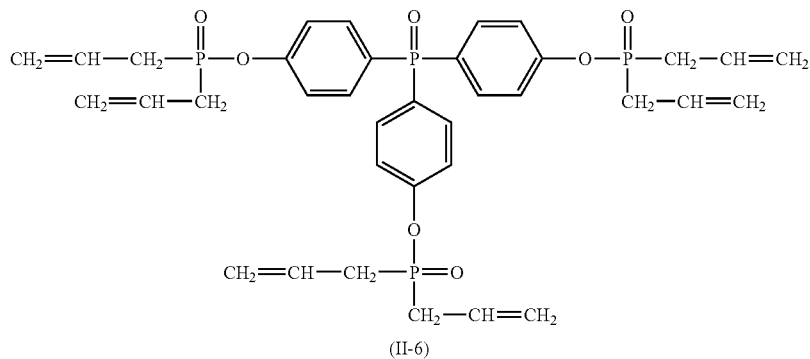
(II-6)

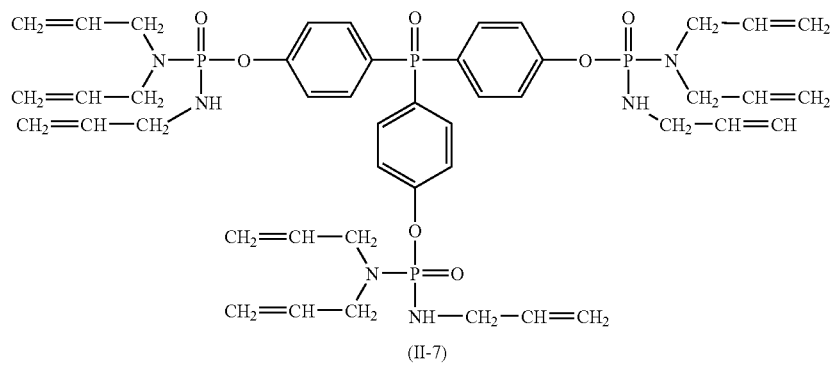
(II-7)
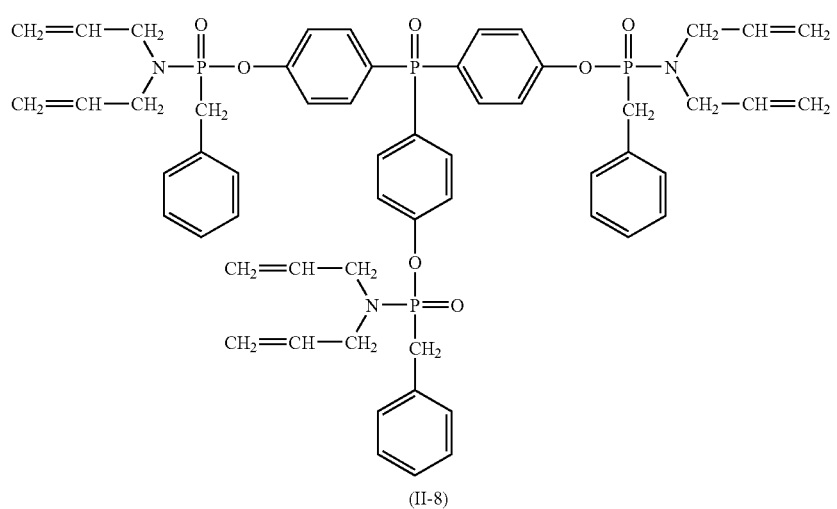
(II-8)
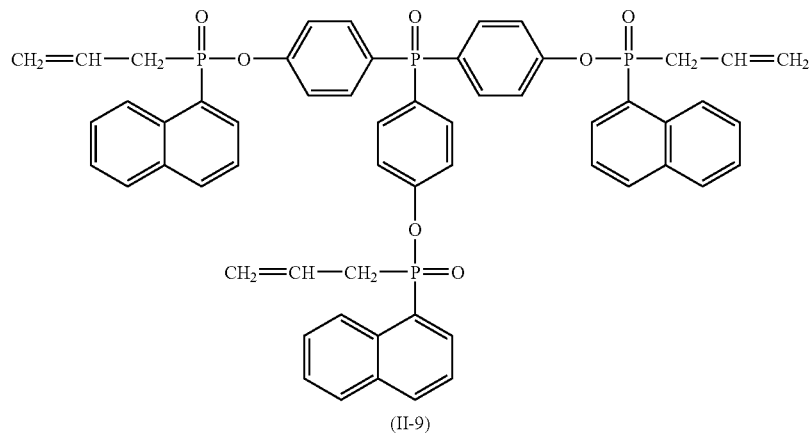
(II-9)

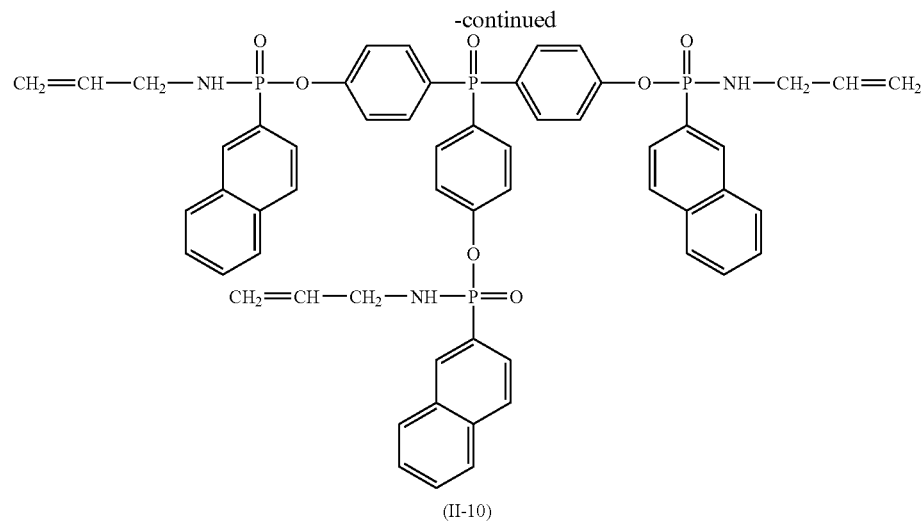
(II-10)
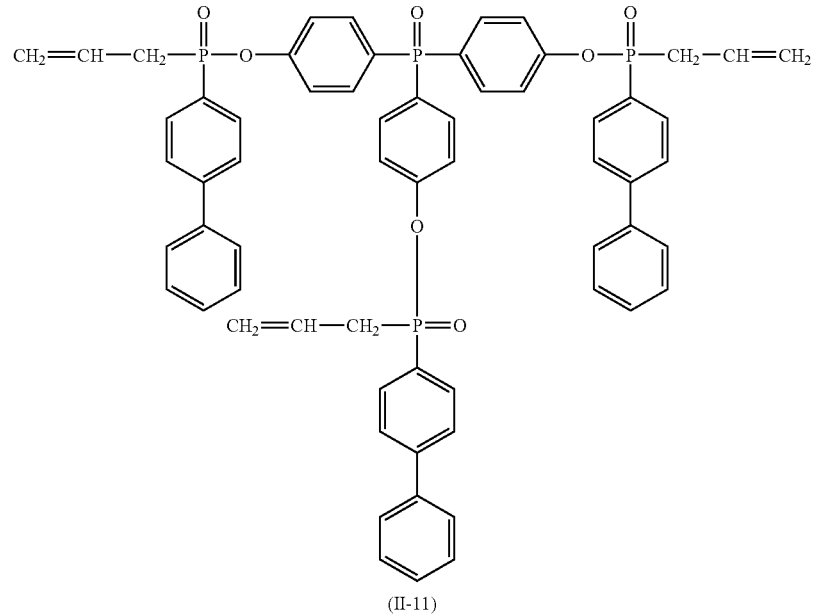
(II-11)
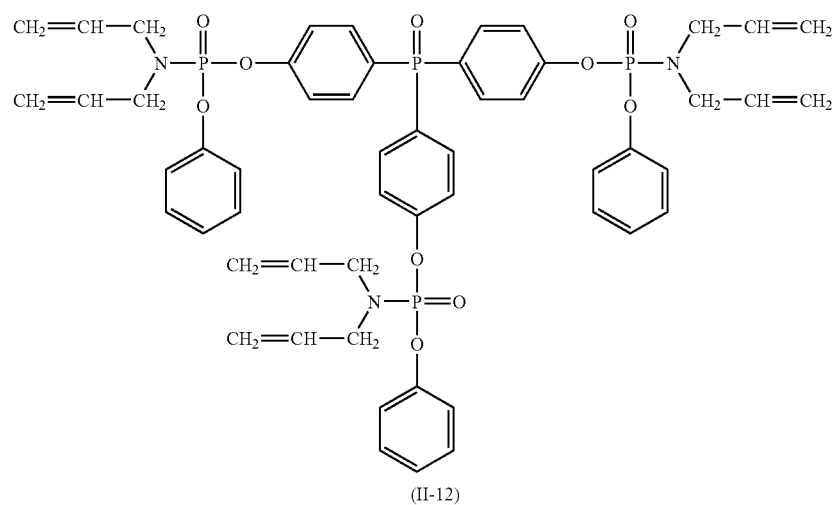
(II-12)

-continued
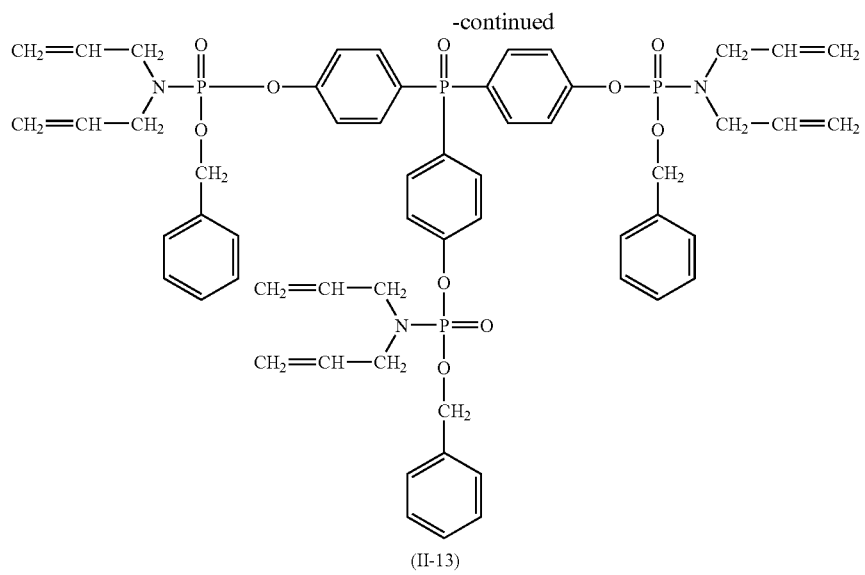
(II-13)
[Chem 14]
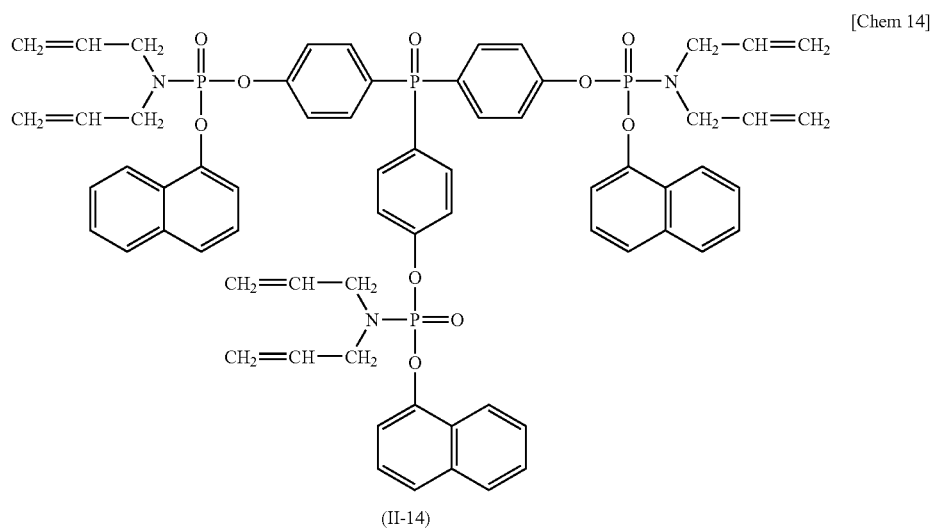
(II-14)
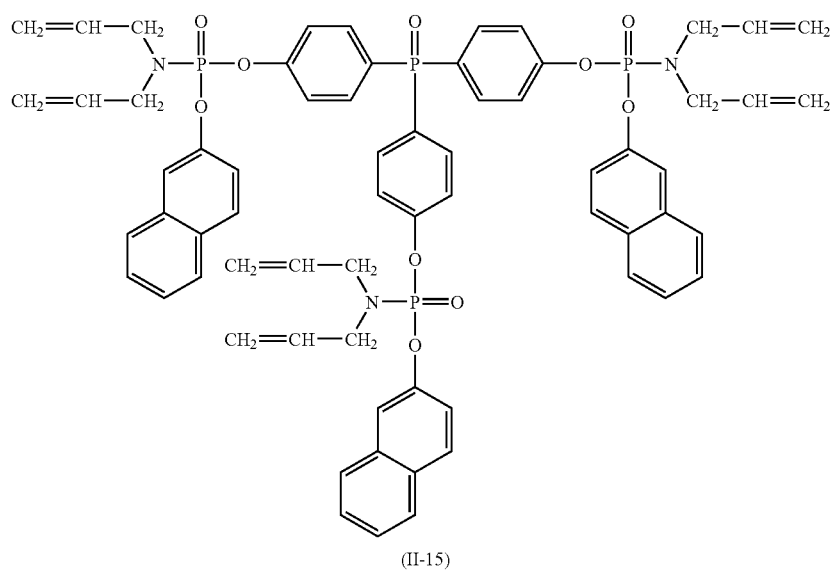
(II-15)

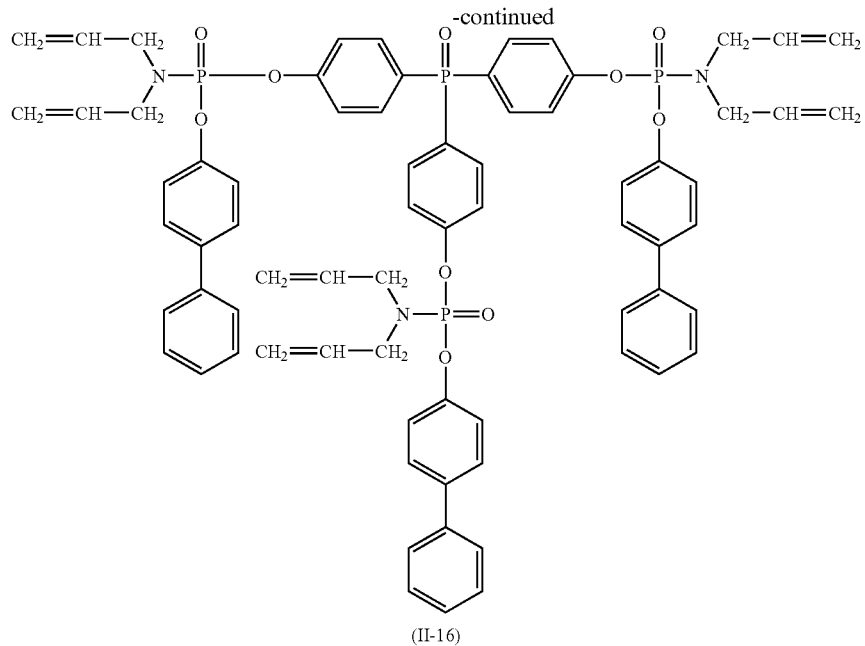

(II-16)

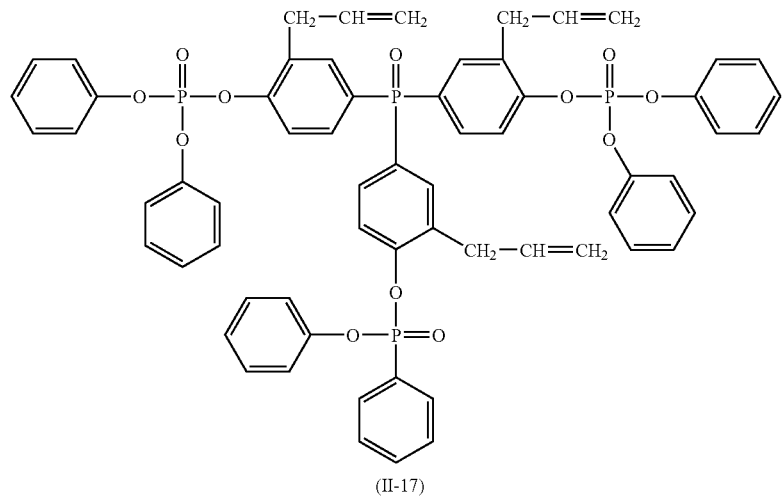

(II-17)

Each of those compounds can be synthesized by, for example, a method involving: synthesizing tris(3-allyl-4-hydroxyphenyl)phosphine oxide or tris(4-hydroxyphenyl) phosphine oxide as a skeleton first; and causing the skeleton to react with phosphonic chloride having a functional group to be required. It should be noted that tris(3-allyl-4-hydroxyphenyl)phosphine oxide or tris(4-hydroxyphenyl)phosphine oxide can be synthesized by: causing a hydroxyl group of 2-allyl-4-bromophenol or of 4-bromophenol to react with chlorotrimethylsilane to thereby provide a form of —OSi(CH$_3$)$_3$; causing the resultant to react with metal lithium to lithiate a bromine position; causing 3 moles of the resultant to react with 1 mole of phosphorus oxychloride; and hydrolyzing the —OSi(CH$_3$)$_3$ portion after the reaction to return the portion to a hydroxyl group.

For example, the compound represented by the formula (II-1) can be synthesized by: synthesizing tris(3-allyl-4-hydroxyphenyl)phosphine oxide as a skeleton first; and causing the skeleton to react with diphenylphosphonic chloride.

Next, a flame-retardant resin processed article using the above-mentioned reactive flame retardant will be described.

A flame-retardant resin processed article of the present invention contains a reactive flame retardant containing an organophosphorus compound represented by the above-mentioned general formula (I) or (II) and a resin. The flame-retardant resin processed article is obtained by: molding a resin composition containing 1 to 20 mass % of the reactive flame retardant with respect to the entirety of the resin composition, or making the resin composition into a coating film; and causing the resin and the reactive flame retardant to react with each other through heating or the application of radiation.

Each of a thermoplastic resin and a thermosetting resin can be used without any particular limitation as a resin to be used in the flame-retardant resin processed article of the present invention.

Examples of the thermoplastic resin include: a polyamide-based resin; a polyester-based resin such as a polybutylene terephthalate resin or polyethylene terephthalate; a polyacryl-based resin; a polyimide-based resin; a polycarbonate resin; a polyurethane-based resin; a polystyrene-based resin such as polystyrene, an acrylonitrile-styrene copolymer, or an acrylonitrile-butadiene-styrene copolymer; a polyacetal-based resin; a polyolefin-based resin; a polyphenylene oxide resin; a polyphenylene sulfide resin; and a polybutadiene resin. Of those, in terms of mechanical characteristics, heat resistance, and the like, a polyamide-based resin, a polybutylene terephthalate resin, a polyethylene terephthalate resin, a polycarbonate resin, a polyacryl-based resin, a polyacetal-based resin, or a polyphenylene oxide resin is preferably used.

Examples of the thermosetting resin include an epoxy resin, a urethane resin, an unsaturated polyester resin, a phenol resin, a urea resin, a melamine resin, an alkyd resin, and a silicone resin. Of those, in terms of mechanical characteristics, heat resistance, and the like, an epoxy resin, a phenol resin, an unsaturated polyester resin, or a urea resin is preferably used.

The content of the above-mentioned reactive flame retardant must be 1 to 20 mass %, and is preferably 1 to 15 mass % with respect to the entirety of the resin composition. When the content of the reactive flame retardant is less than 1 mass %, crosslinking as a result of a reaction between the reactive flame retardant and the resin is insufficient, the mechanical, thermal, and electrical physical properties of a resin processed article to be obtained are insufficient, and no sufficient flame retardance can be obtained. On the other hand, a content of the reactive flame retardant in excess of 20 mass % is not preferable because the amount of the reactive flame retardant is excessive, the unreacted monomer or decomposed gas of the reactive flame retardant may be generated, or an oligomerized one may bleed out, and, further, the mechanical characteristics of a resin processed article to be obtained may reduce.

It is preferable that: the flame-retardant resin processed article of the present invention contain two or more kinds of compounds different from each other in reactivity out of the organophosphorus compounds each represented by the above-mentioned general formula (I) or (II), that is, two or more kinds of organophosphorus compounds different from each other in number of the above-mentioned functional groups in one molecule; and at least one kind of the organophosphorus compounds be a multifunctional reactive flame retardant. The combined use of reactive flame retardants different from each other in number of functional groups can control a reaction rate needed for crosslinking, and can prevent the contraction of a resin composition due to the abrupt progress of a crosslinking reaction. In addition, the use of a multifunctional reactive flame retardant can result in the formation of a uniform, three-dimensional network structure from an organophosphorus compound, and can improve the mechanical strength of the resin processed article against, for example, tension, compression, bending, or an impact.

In addition, the flame-retardant resin processed article of the present invention preferably further contains a reactive flame retardant composed of a cyclic nitrogen-containing compound having at least one unsaturated group at a terminal of the compound (hereinafter referred to as "multifunctional cyclic compound") other than the organophosphorus compound represented by the above-mentioned general formula (I) or (II). In addition, it is more preferable that the content of the reactive nitrogen-containing compound is more preferably 0.5 to 10 parts by mass with respect to 1 part by mass of the organophosphorus compound of the present invention.

Specific examples of the group having an unsaturated group at an end of the multifunctional cyclic compound include a diacrylate, a dimethacrylate, a diallylate, a triacrylate, a trimethacrylate, a triallylate, a tetraacrylate, a tetramethacrylate, and a tetraallylate. Of those, an acrylate such as a diacrylate, a triacrylate, or a tetraacrylate is more preferable in terms of reactivity. Examples of the cyclic nitrogen-containing compound include an isocyanuric ring and a cyanuric ring.

Specific examples of the multifunctional cyclic compound include derivatives of the above-mentioned cyanuric acid or isocyanuric acid, and multifunctional monomer or oligomer such as isocyanuric acid EO-denatured diacrylate, isocyanuric acid EO-denatured triacrylate, and triisocyanuric triacrylate can be exemplified.

In addition, the flame-retardant resin processed article of the present invention preferably contains an addition type flame retardant having no reactivity (hereinafter referred to as "addition type flame retardant") other than the above-mentioned reactive flame retardant. Preferable examples of such addition type flame retardant include: metal hydrates typified by, for example, aluminum hydroxide and magnesium hydroxide; mono-phosphoric acid esters such as triphenyl phosphate and tricresyl phosphate; condensed-phosphoric acid esters such as bisphenol A bis(diphenyl) phosphate and resorcinol bis(diphenyl) phosphate; ammonium polyphosphate; polyphosphoric acid amide; red phosphorus; guanidine phosphate; derivatives of cyanuric acid or of isocyanuric acid; and non-halogen-based flame retardants such as a melamine derivative.

In addition, each of those addition type flame retardants may be used alone, or two or more kinds of them can be used in combination. The content of the addition type flame retardant is preferably 1 to 20 mass %, or more preferably 3 to 15 mass % with respect to the entirety of the resin composition in order that the occurrence of the bleedout of the flame retardant, and reductions in mechanical characteristics of the resin processed article may be prevented.

In addition, the flame-retardant resin processed article of the present invention preferably further contains a crosslinking agent which has no flame retardance but is reactive with the resin. It should be noted that the term "crosslinking agent which has no flame retardance but is reactive with the resin" as used in the present invention refers to a crosslinking agent which has crosslinking property (reactivity) but which itself has no flame retardance. The term excludes a reactive flame retardant having crosslinking property and flame retardance simultaneously like the above-mentioned "cyclic nitrogen-containing compound having at least one unsaturated group at a terminal of the compound".

A multifunctional monomer or oligomer having an unsaturated group at a terminal of its main skeleton can be preferably used as such crosslinking agent, and examples of such crosslinking agent include bifunctional to tetrafunctional compounds represented by the following general formulae (a) to (c). Here, M represents a main skeleton, $R^{11}$ to $R^{14}$ each represent a functional group having a terminal unsaturated group, (a) represents a bifunctional compound, (b) represents a trifunctional compound, and (c) represents a tetrafunctional compound.

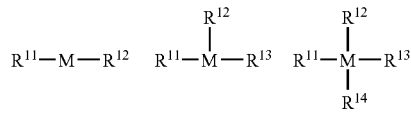

Specific examples thereof include structures represented by the following general formulae in each of which the main skeleton M is an aliphatic alkyl such as a glycerin or a pentaerythritol derivative; an aromatic ring such as trimellitic acid, pyromellitic acid, tetra hydrofuran, or trimethylene trioxane; and bisphenol.

[Chem 17]

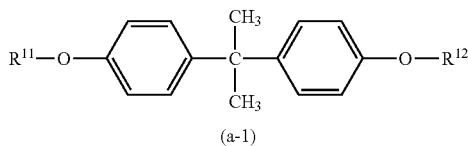

(a-1)

[Chem 18]

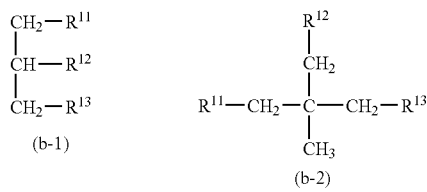

(b-1)    (b-2)

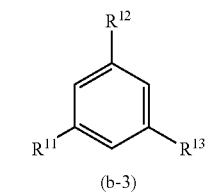    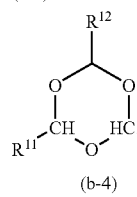

(b-3)    (b-4)

[Chem 19]

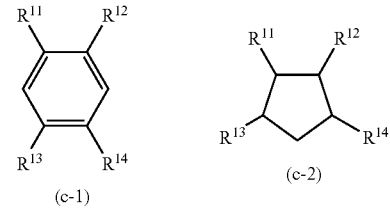

(c-1)    (c-2)

Specific examples of bifunctional monomers or oligomers include diacrylates including bisphenol F-EO-denatured diacrylate, bisphenol A-EO-denatured diacrylate, tripropylene glycol diacrylate, polypropylene glycol diacrylate, polyethylene glycol diacrylate, and pentaerythritol diacrylate monostearate, and dimethacrylates and diallylates thereof.

Further, specific examples of trifunctional monomers or oligomers include triacrylates such as pentaerythritol triacrylate, trimethylolpropane triacrylate, trimethylolpropane PO-denatured triacrylate, and trimethylolpropane EO-denatured triacrylate, and trimethacrylates and triallylates thereof.

Further, specific examples of tetrafunctional monomers or oligomers include ditrimethylolpropane tetraacrylate and pentaerythritol tetraacrylate.

The crosslinking agent is obtained by causing one kind selected from allyl bromide, allyl alcohol, allylamine, methallyl bromide, methallyl alcohol, and methallylamine to be a functional group having an unsaturated group at an end to react with one kind selected from trimellitic acid, pyromellitic acid, tetra hydrofuran tetracarboxylic acid, 1,3,5-trihydroxybenzene, glycerin, pentaerythritol, and 2,4,6-tris(chloromethyl)-1,3,5-trioxane being the main skeleton M.

The content of the crosslinking agent is preferably 0.5 to 10 parts by mass with respect to 1 part by mass of the reactive flame retardant.

In addition, the flame-retardant resin processed article of the present invention may further contain, for example, an inorganic filler, a reinforced fiber, or any one of various additives.

The incorporation of an inorganic filler improves the mechanical strength and dimensional stability of a resin processed article. In addition, the inorganic filler serves as a base substance for adsorbing a reactive flame retardant to uniformly disperse the reactive flame retardant in the resin composition.

Any conventionally known inorganic filler can be used, and representative examples thereof include: metal powders of copper, iron, nickel, zinc, tin, stainless steel, aluminum, gold, silver, and the like; fumed silica; aluminum silicate; calcium silicate; silicic acid; water-containing calcium silicate; water-containing aluminum silicate; glass beads; carbon black; a quartz powder; isinglass; talc; mica; clay; titanium oxide; iron oxide; zinc oxide; calcium carbonate; magnesium carbonate; magnesium oxide; calcium oxide; magnesium sulfate; potassium titanate; and diatomaceous earth. Each of those inorganic fillers may be used alone, or two or more of them may be used in combination. In addition, each of those inorganic fillers may be treated with a conventionally known surface treatment agent. Particularly of those, in the present invention, a laminar clay obtained by laminating silicate layers is preferably used as the inorganic filler. The term "laminar clay obtained by laminating silicate layers" refers to a clay having a structure in which silicate layers each having a thickness of about 1 nm and a length of one side of about 100 nm are laminated. Accordingly, the laminar clay is dispersed into the resin in a nano order to form a hybrid structure with the resin. As a result, the heat resistance, mechanical strength, and the like of the flame-retardant resin processed article are improved. The average particle size of the laminar clay is preferably 100 nm or less. Examples of the laminar clay include montmorillonite, kaolinite, and mica. Of those, montmorillonite is preferable because of its excellent dispersibility. The laminar clay may be surface-treated for improving dispersibility into a resin. Such laminar clay may be a commercially available one, and, for example, "Nanomer" (trade name, manufactured by NISSHOIWAI BENTONITE) or "Somasif" (trade name, manufactured by Co-op Chemical) can be used.

In addition, the content of the inorganic filler is preferably 1 to 45 mass %, or more preferably 1 to 20 mass % with respect to the entirety of the flame-retardant resin processed article. A content of the inorganic filler of less than 1 mass % is not preferable because the mechanical strength of the flame-retardant resin processed article is deficient, and the dimensional stability of the article is insufficient. A content of the inorganic filler in excess of 45 mass % is not preferable because the flame-retardant resin processed article becomes brittle. In addition, when the flame-retardant resin processed article contains laminar clay, the content of the laminar clay is preferably 1 to 10 mass % with respect to the entirety of the flame-retardant resin processed article. It should be noted that the laminar clay may be used alone, or may be used in combination with any other inorganic filler.

The incorporation of the reinforced fibers can improve the mechanical strength and dimensional stability of, for example, a molded article. Examples of the reinforced fibers include glass fibers, carbon fibers, and metal fibers. Glass fibers are preferably used in terms of strength and adhesiveness with the resin or with the inorganic filler. One kind of reinforced fiber may be used alone, or two or more kinds of fibers may be used in combination. The fibers may be treated with a conventionally known surface treatment agent such as a silane coupling agent.

A surface-treated glass fiber is particularly preferably used as the above-mentioned reinforced fiber, and the fiber is more preferably coated with a resin. In this case, adhesiveness with a thermoplastic polymer can be additionally improved.

A conventionally known silane coupling agent can be used as the surface treatment agent to be used for the reinforced fibers, and specific examples thereof include silane coupling agents each having at least one alkoxy group selected from the group consisting of a methoxy group and an ethoxy group and at least one reactive functional group selected from the group consisting of an amino group, a vinyl group, an acrylic group, a methacrylic group, an epoxy group, a mercapto group, a halogen atom, and an isocyanate group.

The resin for coating to be used for the reinforced fiber is not particularly limited, and examples thereof include a urethane resin and an epoxy resin.

The content of the reinforced fibers is preferably 5 to 50 mass %, or more preferably 10 to 45 mass % with respect to the entirety of the flame-retardant resin processed article. A content of less than 5 mass % is not preferable because the mechanical strength of the flame-retardant resin processed article reduces and the dimensional stability thereof becomes insufficient. A content in excess of 50 mass % is not preferable either because it becomes difficult to process the resin.

The flame-retardant resin processed article of the present invention may be added with any one of common various addition components except those described above such as a crystal nucleating agent, a colorant, an antioxidant, a release agent, a plasticizer, a heat stabilizer, a lubricant, and a UV inhibitor to the extent that physical properties such as heat resistance, weatherability, and impact resistance as objects of the present invention are not significantly impaired. In addition, as described later, a UV initiator or the like can be used when the resin and the reactive flame retardant are allowed to react with each other due to ultra violet light.

The colorant is not particularly limited, but is preferably one that does not show color fading when irradiated with a radiation to be described later. For example, an inorganic pigment such as blood red, iron black, carbon, or chrome yellow, or a metal complex such as phthalocyanine is preferably used.

The flame-retardant resin processed article of the present invention is obtained by molding or film-coating the resin composition and then reacting the resin with the reactive flame retardant by heating or irradiation with a radiation.

The resin composition is molded by using a conventionally known method. For example, in the case of a resin composition containing a thermoplastic resin, the thermoplastic resin and a reactive flame retardant are melted and kneaded to produce a pellet. Then, the pellet can be molded by using a conventionally known method such as injection molding, extrusion molding, vacuum molding, or inflation molding. The melding and kneading can be performed using a general melting and kneading processing machine such as a monoaxial or biaxial extruder, a Banbury mixer, a kneader, or a mixing roll. A kneading temperature can be appropriately selected depending on the kind of the thermoplastic resin. For example, in the case of a polyamide-based resin, the kneading is preferably performed at 240 to 280° C. Molding conditions can be appropriately set and are not particularly limited. At this stage, crosslinking does not advance at all, so an extra spool portion at the time of molding can be recycled as a thermoplastic resin.

On the other hand, in the case of a thermosetting resin, as in the case of the above, the thermosetting resin and a reactive flame retardant are melted and kneaded to produce a pellet. Then, the pellet can be molded by using, for example, a conventionally known method such as injection molding, compression molding, or transfer molding.

In the case of preparing a coating film, the resin composition may be applied as it is. Alternatively, the resin composition may be appropriately diluted with a solvent or the like to prepare a solution or suspension that can be applied, and the solution or suspension may be dried by using a conventionally known method to prepare a coating film. A coating method such as roller coating, spraying, immersion, or spin coating can be used for preparing a coating film, and a method to be used is not particularly limited.

In the resin composition, an unsaturated bond at an end of the reactive flame retardant reacts with the resin to prompt a crosslinking reaction as a result of heating or irradiation with a radiation, so a component of flame retardant is stably present in the resin.

When heating is employed as means for reacting the reactive flame retardant and the resin, the resin and the reactive flame retardant are reacted at a temperature higher than the temperature at which the resin is molded by preferably 5° C. or higher, or more preferably 10° C. or higher.

When a radiation is used as means for crosslinking, an electron beam, an α ray, a γ ray, an X-ray, ultra violet light, or the like can be used. The term "radiation" used in the present invention refers to a radiation in a broad sense, and specifically includes an electromagnetic wave such as an X-ray or ultra violet light in addition to a particle beam such as an electron beam or an α ray.

The irradiation is preferably performed with an electron beam or a γ ray out of the foregoing. A conventionally known electron accelerator or the like can be used for irradiation with an electron beam, and an accelerating energy of 2.5 MeV or more is preferable. Irradiation equipment using a conventionally known cobalt 60 radiation source or the like can be used for irradiation with a γ ray.

Irradiation equipment using a conventionally known cobalt 60 radiation source or the like can be used for irradiation with a γ ray. A γ ray is preferable because it has stronger permeability than that of an electron beam, so irradiation can be performed uniformly. However, the γ ray has strong radiation intensity, so the dose of the ray must be controlled in order to prevent excessive irradiation.

The irradiation dose of a radiation is preferably 10 kGy or more, or more preferably 10 to 45 kGy. An irradiation dose in this range provides a resin processed article excellent in the above-mentioned physical properties owing to crosslinking. An irradiation dose of less than 10 kGy is not preferable because the formation of a three-dimensional network structure due to crosslinking may be nonuniform and an unreacted crosslinking agent may bleed out. An irradiation dose larger than 45 kGy is not preferable either because the internal strain of the resin processed article due to an oxidation decomposition product remains to cause deformation, contraction, and the like.

The flame-retardant resin processed article of the present invention thus produced is excellent in mechanical characteristics, electrical characteristics, dimensional stability, and moldability in addition to heat resistance and flame retardance. Therefore, the resin processed article can be suitably used for an electrical or electronic component in which high levels of heat resistance and flame retardance are required, and for an automobile part or an optical part such as: a member for supporting a contact of an electromagnetic switch, a breaker, or the like; a substrate such as a printed board; a package for an integrated circuit; or a housing for an electrical component.

Specific examples of such electrical or electronic component include: a receiving board; a distribution board; an electromagnetic switch; a breaker; a transformer; an electromagnetic contactor; a circuit protector; a relay; a transformer; various sensors; various motors; and semiconductor devices such as a diode, a transistor, and an integrated circuit.

The resin processed article can be suitably used for an automobile part such as: a cooling fan; a bumper; a brake cover; an interior part such as a panel; a sliding part; a sensor; or a motor.

The resin processed article can be used not only as a molded article but also as a flame-retardant coating film for the molded article, a fiber, or the like.

In addition, excellent heat resistance and excellent flame retardance can be imparted when the resin processed article is used for, for example, sealing, covering, and insulating the above-mentioned electronic or electrical component such as a semiconductor device. That is, for example, the resin composition is sealed to cure the resin, and the above-mentioned reaction by heating or irradiation with a radiation is performed, whereby the resin processed article can be used as a flame-retardant sealing compound for sealing an electronic component or an electrical element such as a semiconductor chip or a ceramic capacitor. Sealing can be performed by casting, potting, transfer molding, injection molding, compression molding, or the like. An electronic or electrical component to be sealed is not particularly limited, and examples thereof include a liquid crystal, an integrated circuit, a transistor, a thyristor, a diode, and a capacitor.

EXAMPLES

Hereinafter, the present invention will be described in more detail by way of examples. However, the present invention is not limited to the examples.

<Synthesis of Organophosphorus Compound>

Example 1

Synthesis of Compound (I-1)

43.28 g (205 mmol) of phenylphosphoric dichloride and 200 ml of distilled ethyl acetate were loaded into a 500-ml four-necked flask equipped with a reflux pipe with a dry pipe, a mechanical stirring device, a nitrogen gas introducing pipe, and a dropping funnel. The mixture was placed under nitrogen, and was stirred at 0 to 5° C. During the stirring, the mixed liquid of 19.89 g (205 mmol) of diallylamine and 41.52 g (410 mmol) of triethylamine was slowly added to the mixture from the dropping funnel. After the completion of the dropping, the resultant was subjected to a reaction at room temperature for 3 hours and then at 70° C. for 12 hours. After the resultant had been cooled, triethylamine hydrochloride salt was removed by filtration, and the solution was condensed under reduced pressure so that the solvent and excessive amine were removed. After that, the remainder was distilled under reduced pressure so that a fraction at 144 to 146° C./5 mmHg was collected. Thus, 47.73 g of phenylphosphoric mono(N,N-diallyl)amide monochloride (hereinafter referred to as "POPAC") were obtained (in 85% yield). It should be noted that infrared absorption spectrometry, NMR, and TOF-mass spectrometry confirmed that the compound was POPAC.

Infrared absorption spectrometry (cm$^{-1}$): $v_{(C=C)}$ 1635, $v_{(ring)}$ 1604, 1495, $v_{(P=O, POC)}$ 1280, 1195, 1040, $v_{(CN)}$ 945

$^1$H-NMR spectrometry (δ, ppm): phenyl-H 7.15 (2H), 7.33 (3H), —CH= 5.55 (2H), —CH$_2$— 5.10 (4H), =CH$_2$ 3.50 (4H)

TOF-mass spectrometry (M/Z): 273 (calculated molecular weight=271.7)

Next, 250 ml of dimethylformamide (hereinafter referred to as "DMF"), 30.64 g (100 mmol) of a phenol resin represented by the following formula (d), and 4.8 g (200 mmol) of sodium hydride were loaded into a 500-ml four-necked flask equipped with the same devices as those described above. The mixture was placed under nitrogen, and was stirred. Once nearly no generated hydrogen bubbles had been observed, the mixture was heated to 80° C., and was subjected to a reaction for 2 hours. After that, the resultant was cooled to 0 to 5° C. During the cooling, the mixed liquid of 54.35 g (200 mmol) of POPAC and 100 ml of a DMF solution was slowly added to the resultant from a dropping funnel, and the whole was subjected to a reaction at the temperature for 3 hours and then at 60° C. for 12 hours. After that, the solvent was removed by distillation under reduced pressure until the volume of the resultant was reduced by a factor of about 3. The resultant viscous liquid was dropped to 3 L of water which were being vigorously stirred, and the precipitated pale yellow wax-like substance was collected. After having been washed with water, the substance was dried at 60° C. under reduced pressure and heat, whereby 75.2 g of a target compound were obtained (in 97% yield).

The results of the infrared absorption spectrometry, NMR, and TOF-mass spectrometry of the compound were as described below, and the structure of Compound (I-1) shown above was identified.

Infrared absorption spectrometry (cm$^{-1}$): $v_{(C=C)}$ 1635, $v_{(ring)}$ 1604, 1495, $v_{(P=O, POC)}$ 1280, 1195, 1040, $v_{(CN)}$ 945, $v_{(OH)}$ 3380

$^1$H-NMR spectrometry (δ, ppm): —OH 9.2 (1H), phenyl-H 6.85-7.55 (22H), —CH= 5.60 (4H), allyl-CH$_2$— 5.15 (8H), =CH$_2$ 3.50 (8H), CH$_3$ 1.95 (3H)

TOF-mass spectrometry (M/Z): 779 (calculated molecular weight=776.82)

[Chem 20]

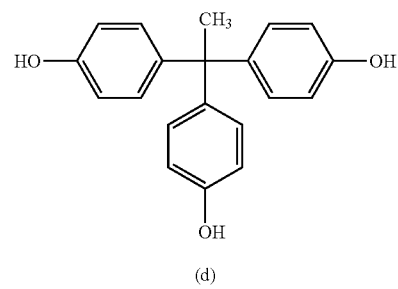

(d)

Example 2

Synthesis of Compound (I-2)

The same operation as that of Example 1 was performed except that: 39.97 g (205 mmol) of phenylphosphonic dichloride were used instead of phenylphosphoric dichloride; and a fraction at 122 to 124° C./5 mmHg was collected by distillation under reduced pressure. Thus, 43.50 g of phenylphosphonic mono(N,N-diallyl) amide monochloride (hereinafter referred to as "PPAC") were obtained (in 83% yield). It should be noted that infrared absorption spectrometry, NMR, and TOF-mass spectrometry confirmed that the compound was PPAC.

Infrared absorption spectrometry (cm$^{-1}$): $v_{(C=C)}$ 1635, $v_{(ring)}$ 1604, 1495, $v_{(P=O, POC)}$ 1280, $v_{(CN)}$ 945

$^1$H-NMR spectrometry (δ, ppm): phenyl-H 6.85 (2H), 7.10 (3H), —CH= 5.45 (2H), —CH$_2$— 4.95 (4H), =CH$_2$ 3.35 (4H)

TOF-mass spectrometry (M/Z): 257 (calculated molecular weight=255.7)

Next, 250 ml of DMF, 42.55 g (100 mmol) of a phenol resin represented by the following formula (e), and 7.05 g (300 mmol) of sodium hydride were loaded into a 500-ml four-necked flask equipped with the same devices as those described above. The mixture was placed under nitrogen, and was stirred. Once nearly no generated hydrogen bubbles had been observed, the mixture was heated to 80° C., and was subjected to a reaction for 2 hours. After that, the resultant was cooled to 0 to 5° C. During the cooling, the mixed liquid of 76.73 g (300 mmol) of PPAC and 100 ml of DMF was slowly added to the resultant from a dropping funnel, and the whole was subjected to a reaction at the temperature for 3 hours and then at 60° C. for 12 hours. After that, the solvent was removed by distillation under reduced pressure until the volume of the resultant was reduced by a factor of about 3. The resultant viscous liquid was dropped to 3 L of water which were being vigorously stirred, and the precipitated pale yellow wax-like substance was collected. After having been washed with water, the substance was dried at 60° C. under reduced pressure and heat, whereby 104.2 g of a target compound were obtained (in 96% yield).

The results of the infrared absorption spectrometry, NMR, and TOF-mass spectrometry of the compound were as described below, and the structure of Compound (I-2) shown above was identified.

Infrared absorption spectrometry (cm$^{-1}$): $v_{(C=C)}$ 1635, $v_{(ring)}$ 1604, 1495, $v_{(P=O, POC)}$ 1280, 1195, 1040, $v_{(CN)}$ 945

$^1$H-NMR spectrometry (δ, ppm): phenyl-H 6.85-7.55 (31H), —CH= 5.60 (6H), allyl-CH$_2$— 5.15 (12H), =CH$_2$ 3.50 (12H), CH$_3$ 1.6-1.85 (9H)

TOF-mass spectrometry (M/Z): 1085 (calculated molecular weight=1083.2)

[Chem 21]

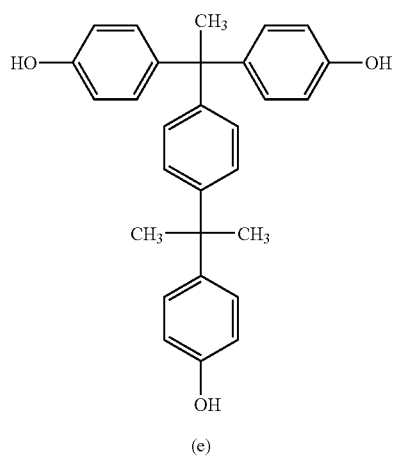

(e)

Example 3

Synthesis of Compound (I-3)

153.32 g (1.00 mol) of phosphorus oxychloride and 200 ml of distilled chloroform were loaded into a 500-ml four-necked flask equipped with the same devices as those of Example 1. The mixture was placed under nitrogen, and was stirred at 0 to 5° C. During the stirring, a mixed liquid prepared by dissolving 30.64 g (100 mmol) of a phenol resin represented by the above formula (d) and 41.52 g (410 mmol) of triethylamine in 100 ml of chloroform was slowly added to the mixture from a dropping funnel. After the completion of the dropping, the resultant was subjected to a reaction at room temperature for 3 hours and then at 70° C. for 12 hours. After the resultant had been cooled, triethylamine hydrochloride salt was removed by filtration, and the solution was removed by distillation under reduced pressure so that the solvent and excessive amine were removed. After that, 200 ml of tetra hydrofuran (hereinafter referred to as "THF") were added to the remainder, and the resultant solution was returned to the foregoing reactor.

Next, 200 ml of a solution of 54.93 g (300 mmol) of potassium α-naphthoxide in THF were slowly added to the solution from the dropping funnel, and the whole was subjected to a reaction at room temperature for 3 hours and then under boiling point reflux for 6 hours. After the resultant had been returned to room temperature, the mixed liquid of 22.82 g (400 mmol) of allylamine and 40.50 g (400 mmol) of triethylamine was slowly added to the resultant from the dropping funnel, and the whole was subjected to a reaction at room temperature for 3 hours and then under boiling point reflux for 12 hours. After that, the resultant was condensed under reduced pressure so that its volume was reduced by a factor of about 3. After that, the resultant viscous liquid was dropped to 3 L of water which were being vigorously stirred, and the precipitated pale yellow wax-like substance was collected. After having been washed with water, the substance was dried at 60° C. under reduced pressure and heat, whereby 98.4 g of a target compound were obtained (in 81% yield).

The results of the infrared absorption spectrometry, NMR, and TOF-mass spectrometry of the compound were as described below, and the structure of Compound (I-3) shown above was identified.

Infrared absorption spectrometry (cm$^{-1}$): $v_{(NH)}$ 3360, 1620, $v_{(C=C)}$ 1635, $v_{(ring)}$ 1604, 1495, $v_{(P=O, POC)}$ 1280, 1195, 1040, $v_{(CN)}$ 945

$^1$H-NMR spectrometry (δ, ppm): allyl-H 6.85-7.55 (33H), —CH= 5.60 (3H), allyl-CH$_2$— 5.15 (6H), >NH 3.65 (3H), =CH$_2$ 3.50 (6H), CH$_3$ 1.85 (3H)

TOF-mass spectrometry (M/Z): 1044 (calculated molecular weight=1042)

Example 4

Synthesis of Compound (I-4)

76.67 g (0.50 mol) of phosphorus oxychloride and 200 ml of THF were loaded into a 1,000-ml four-necked flask equipped with the same devices as those of Example 1. The mixture was placed under nitrogen, and was stirred at 0 to 5° C. During the stirring, 500 ml of a 1.0-mol/l solution of allyl magnesium chloride in THF were slowly added to the mixture from a dropping funnel, and the whole was subjected to a reaction at room temperature for 3 hours and then at 60° C. for 10 hours. After that, the solvent was removed by distillation under reduced pressure at temperatures equal to or lower than room temperature so as to be a solution in chloroform. The produced precipitate of magnesium chloride was removed by filtration, and the solution was condensed under reduced pressure to adjust to 300 ml. Then the resultant solution was returned to the foregoing reactor.

Next, a mixed liquid prepared by dissolving 30.64 g (100 mmol) of a phenol resin represented by the above formula (d)

and 41.52 g (410 mmol) of triethylamine in 200 ml of chloroform was slowly added to the solution, and the whole was subjected to a reaction at room temperature for 3 hours and then at 60° C. for 12 hours. After the resultant had been cooled, the precipitate was removed by filtration, and the solution was dried and solidified under reduced pressure so that an excessive reagent and the solvent were removed. The total amount of the residue was dissolved in 400 ml of chloroform, and the resultant solution was returned to the foregoing reactor. A mixed liquid prepared by dissolving 53.57 g (500 mmol) of benzylamine and 50.64 g (500 mmol) of triethylamine in 200 ml of chloroform was slowly added to the solution from the dropping funnel, and the whole was subjected to a reaction at room temperature for 3 hours and then at 60° C. for 12 hours. A wax-like substance that was obtained by removing the excessive reagent and the solvent under reduced pressure was dispersed in 3 L of water, and the whole was stirred. The precipitated pale yellow solid was collected by filtration, washed with water, and dried, whereby 79.6 g of a target compound were obtained (in 94% yield).

The results of the infrared absorption spectrometry, NMR, and TOF-mass spectrometry of the compound were as described below, and the structure of Compound (I-4) shown above was identified.

Infrared absorption spectrometry (cm$^{-1}$): $v_{(NH)}$ 3360, 1620, $v_{(C=C)}$ 1635, $v_{(ring)}$ 1604, 1495, $v_{(P=O, POC)}$ 1280, 1195, 1040, $v_{(CN)}$ 945

$^1$H-NMR spectrometry (δ, ppm): allyl-H 6.85-7.55 (27H), —CH= 5.60 (3H), allyl-CH$_2$— 5.15 (6H), benzyl-CH$_2$ 4.3 (6H), >NH 3.65 (3H) =CH$_2$ 3.50 (6H), CH$_3$ 1.85 (3H)

TOF-mass spectrometry (M/Z): 888 (calculated molecular weight=885.92)

Example 5

Synthesis of Compound (I-5)

30.64 g (100 mmol) of a phenol resin represented by the above formula (d), 250 ml of DMF, and 2.35 g (100 mmol) of sodium hydride were loaded into a 500-ml four-necked flask equipped with the same devices as those of Example 1. The mixture was placed under nitrogen, and was stirred. Once nearly no generated hydrogen bubbles had been observed, the mixture was heated to 80° C., and was subjected to a reaction for 2 hours. After that, the resultant was cooled to 0 to 5° C. During the cooling, the mixed liquid of 25.58 g (100 mmol) of PPAC (see Example 2) and 100 ml of a DMF solution was slowly added to the resultant from a dropping funnel, and the whole was subjected to a reaction at the temperature for 3 hours and then at 60° C. for 12 hours. After that, the solvent was removed by distillation under reduced pressure until the volume of the resultant was reduced by a factor of about 3. The resultant viscous liquid was dropped to 3 L of water which were being vigorously stirred, and the precipitated pale yellow wax-like substance was collected. After having been washed with water, the substance was dried at 60° C. under reduced pressure and heat, whereby 104.2 g of a target compound were obtained (in 96% yield).

The results of the infrared absorption spectrometry, NMR, and TOF-mass spectrometry of the compound were as described below, and the structure of Compound (I-5) shown above was identified.

Infrared absorption spectrometry (cm$^{-1}$): $v_{(OH)}$ 3380, $v_{(C=C)}$ 1635, $v_{(ring)}$ 1604, 1495, $v_{(P=O, POC)}$ 1280, 1195, 1040, $v_{(CN)}$ 945

$^1$H-NMR spectrometry (δ, ppm): —OH 9.35 (2H), phenyl-H 6.85-7.55 (17H), —CH= 5.60 (2H), allyl-CH$_2$— 5.15 (4H), =CH$_2$ 3.50 (4H), CH$_3$ 1.85 (3H)

TOF-mass spectrometry (M/Z): 528 (calculated molecular weight=525.6)

Example 6

Synthesis of Compound (I-6)

250 ml of DMF, 30.64 g (100 mmol) of a phenol resin represented by the above formula (d), and 4.8 g (200 mmol) of sodium hydride were loaded into a four-necked flask equipped with the same devices as those of Example 1. The mixture was placed under nitrogen, and was stirred. Once nearly no generated hydrogen bubbles had been observed, the mixture was heated to 80° C., and was subjected to a reaction for 2 hours. After that, the resultant was cooled to 0 to 5° C. During the cooling, the mixed liquid of 27.17 g (100 mmol) of POPAC (see Example 1) and 100 ml of a DMF solution was slowly added to the resultant from a dropping funnel, and the whole was subjected to a reaction at the temperature for 3 hours and then at 60° C. for 12 hours. Subsequently, the resultant was stirred at 0 to 5° C. During the stirring, under nitrogen, a solution prepared by dissolving 53.7 g (200 mmol) of diphenylphosphoric chloride in 100 ml of DMF was slowly added to the resultant from the dropping funnel. After the completion of the dropping, the resultant was subjected to a reaction at the temperature for 3 hours, then at room temperature for 6 hours, and then at 80° C. for 24 hours. After that, the solvent was removed by distillation under reduced pressure until the volume of the resultant was reduced by a factor of about 3. The resultant viscous liquid was dropped to 3 L of water which were being vigorously stirred, and the precipitated pale yellow wax-like substance was collected. After having been washed with water, the substance was dried at 60° C. under reduced pressure and heat, whereby 91.5 g of a target compound were obtained (in 91% yield).

The results of the infrared absorption spectrometry, NMR, and TOF-mass spectrometry of the compound were as described below, and the structure of Compound (I-6) shown above was identified.

Infrared absorption spectrometry (cm$^{-1}$): $v_{(C=C)}$ 1635, $v_{(ring)}$ 1604, 1495, $v_{(P=O, POC)}$ 1280, 1195, 1040, $v_{(CN)}$ 945 ($v_{(OH)}$ 3200 disappeared)

$^1$H-NMR spectrometry (δ, ppm): phenyl-H 6.85-7.55 (37H), —CH= 5.60 (2H), allyl-CH$_2$— 5.15 (4H), =CH$_2$ 3.50 (4H), CH$_3$ 1.85 (3H)

TOF-mass spectrometry (M/Z): 1008 (calculated molecular weight=1005.92)

Example 7

Synthesis of Compound (II-1)

21.3 g (100 mmol) of 2-allyl-4-bromophenol, 12.1 g (120 mmol) of triethylamine (hereinafter referred to as "TEA"), and 120 ml of distilled tetra hydrofuran (hereinafter referred to as "THF") were loaded into a 300-ml four-necked flask equipped with a reflux pipe with a calcium chloride dry pipe, a dropping funnel, a nitrogen gas introducing pipe, and a mechanical stirring device. The mixture was placed under nitrogen, and was stirred at 0 to 5° C. During the stirring, 11.0 g (120 mmol) of chlorotrimethylsilane were slowly added to the mixture from the dropping funnel. After the completion of the dropping, the resultant was subjected to a reaction at the temperature for 1 hour and then at room temperature for 6 hours. After that, the solvent, excessive trimethylamine, and excessive chlorotrimethylsilane were removed by condensation under reduced pressure, and the residue was washed with water and dried. Thus, 2-allyl-4-bromo-1-trimethylsiloxybenzene was quantitatively obtained.

Next, the total amount of the product obtained in the foregoing step (2-allyl-4-bromo-1-trimethylsiloxybenzene) was loaded into the same four-necked flask as that described above. 150 ml of distilled THF were added to the flask, and the mixture was placed under nitrogen. While the mixture was stirred, 1.39 g (200 mmol) of a metal lithium strip were gradually added to the mixture in order that a mild boiling point reflux state due to heat of reaction might be maintained. After the completion of the addition, the resultant was subjected to a reaction for 8 hours. After that, excessive metal lithium was removed, whereby a 2-allyl-4-lithio-1-trimethylsiloxybenzene solution was quantitatively obtained.

Next, 15.3 g (100 mmol) of phosphorus oxychloride and 100 ml of distilled THF were loaded into the same four-necked flask as that described above. While the mixture was stirred at 0 to 5° C., the total amount of the solution obtained in the foregoing step (2-allyl-4-lithio-1-trimethylsiloxybenzene) was slowly added to the mixture from a dropping funnel under nitrogen, and the whole was subjected to a reaction at the temperature for 3 hours and then at room temperature for 12 hours. After that, 30 ml of 1 N hydrochloric acid were added to the resultant, and the whole was stirred at 50° C. for 3 hours. The solvent was condensed under reduced pressure. The solution residue was washed with water and hexane, and was recrystallized from methanol, whereby 41.1 g of a white, needle-like compound [tris(3-allyl-4-hydroxyphenyl)phosphine oxide (hereinafter referred to as "AHP")] were obtained (in 92% yield) It should be noted that elemental analysis and TOF-mass spectrometry confirmed that the compound was AHP.

Element Assay: C; 72.77% (72.62%), H; 6.04% (6.11%), O; 14.22% (14.33%), P; 6.97% (6.94%)

TOF-mass spectrometry (M/Z): 448 (calculated molecular weight=446.51)

Then, 22.3 g (50.0 mmol) of AHP, 20.2 g (200 mmol) of TEA, and 150 ml of distilled dimethylformamide (hereinafter referred to as "DMF") were loaded into the same four-necked flask as that described above. The mixture was placed under nitrogen, and was stirred at 0 to 5° C. During the stirring, a solution prepared by dissolving 34.0 g (150 mmol) of diphenylphosphonic chloride in 100 ml of DMF was slowly added to the mixture from a dropping funnel. After the completion of the dropping, the resultant was subjected to a reaction at the temperature for 3 hours, then at room temperature for 6 hours, and then at 80° C. for 24 hours. After that, the resultant was dried and solidified under reduced pressure, and was then dissolved in chloroform. The resultant was washed with water, and a chloroform phase was dehydrated with anhydrous sodium sulfate, filtrated, and dried and solidified under reduced pressure, whereby 51.3 g of a target compound were obtained (in 91% yield).

The results of the infrared absorption spectrometry, NMR, and TOF-mass spectrometry of the compound were as described below, and the structure of Compound (II-1) shown above was identified.

Infrared absorption spectrometry (cm$^{-1}$): $v_{(CH2=CH)}$ 1625, $v_{(ring)}$ 1604, 1500, $v_{(P=O)}$ 1200-1300, $v_{(P-O-C)}$ 1210, 950 ($v_{(OH)}$ 3200 disappeared)

$^1$H-NMR spectrometry (δ, ppm): phenyl C—H 7.0-7.5 (39H), allyl C—H 3.5-4.0, 5.1-6.0 (15H)

TOF-mass spectrometry (M/Z): 1049, 1050, 1051 (calculated molecular weight=1047.01)

Example 8

Synthesis of Compound (II-2)

94.95 g (500 mmol) of phenylphosphonic dichloride and 200 ml of THF were loaded into a 300-ml four-necked flask equipped with the same devices as those of Example 7. The mixture was placed under nitrogen, and was stirred at 0 to 5° C. During the stirring, the mixed liquid of 48.6 g (500 mmol) of diallylamine and 50.5 g (500 mmol) of TEA was slowly added to the mixture from a dropping funnel. After the completion of the dropping, the resultant was subjected to a reaction at the temperature for 6 hours and then at room temperature for 24 hours. Amine hydrochloride salt was removed by filtration, and the remainder was condensed under reduced pressure. After that, the resultant was distilled under reduced pressure so that a component at 176 to 180° C./4 mmHg was collected. Thus, 108.5 g of phenylphosphonic mono(N,N-diallyl)amide monochloride (hereinafter referred to as "PPAC") were obtained (in 85% yield).

22.3 g (50.0 mmol) of AHP (see Example 7), 20.2 g (200 mmol) of TEA, and 100 ml of distilled dimethylformamide (DMF) were loaded into the same four-necked flask as that described above. The mixture was placed under nitrogen, and was stirred at 0 to 5° C. During the stirring, a solution prepared by dissolving 12.8 g (50.0 mmol) of PPAC in 50 ml of DMF was slowly added to the mixture from a dropping funnel. After the completion of the dropping, the resultant was subjected to a reaction at the temperature for 3 hours, then at room temperature for 6 hours, and then at 80° C. for 24 hours. Subsequently, the resultant was stirred at 0 to 5° C. During the stirring, under nitrogen, a solution prepared by dissolving 26.9 g (100 mmol) of diphenylphosphoric chloride in 100 ml of DMF was slowly added to the resultant from the dropping funnel. After the completion of the dropping, the resultant was subjected to a reaction at the temperature for 3 hours, then at room temperature for 6 hours, and then at 80° C. for 24 hours. After that, the resultant was dried and solidified under reduced pressure, and was then dissolved in chloroform. The resultant was washed with water, and a chloroform phase was dehydrated with anhydrous sodium sulfate, filtrated, and dried and solidified under reduced pressure, whereby 48.5 g of a target compound were obtained (in 93% yield).

The results of the infrared absorption spectrometry, NMR, and TOF-mass spectrometry of the compound were as described below, and the structure of Compound (II-2) shown above was identified.

Infrared absorption spectrometry (cm$^{-1}$): $v_{(CH2=CH)}$ 1625, $v_{(ring)}$ 1602, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (34H), allyl C—H 3.4-4.1, 5.1-6.1 (25H)

TOF-mass spectrometry (M/Z): 1132, 1133, 1134 (calculated molecular weight=1130.06)

Example 9

Synthesis of Compound (II-3)

29.53 g of tris(4-hydroxyphenyl)phosphine oxide (hereinafter referred to as "HPP") were obtained (in 90.5% yield) in the same manner as in Example 7 except that 17.3 g (mmol) of 4-bromophenol were used instead of 2-allyl-4-bromophenol. It should be noted that elemental analysis and TOF-mass spectrometry confirmed that the compound obtained in the foregoing step was HPP.

Element Assay: C, 66.16% (66.25%), H, 4.92% (4.84%), O; 19.62% (19.61%), P; 9.30% (9.50%)

TOF-mass spectrometry (M/Z): 328 (calculated molecular weight=326.30)

Next, 46.0 g (300 mmol) of phosphorus oxychloride and 100 ml of THF were loaded into a 300-ml four-necked flask equipped with the same devices as those described above. The mixture was placed under nitrogen, and was stirred at 0 to 5° C. During the stirring, a solution prepared by dissolving 16.3 g (50.0 mmol) of HPP and 10.1 g (100 mmol) of TEA in 100 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive phosphorus oxychloride were removed by distillation under reduced pressure, whereby tris[(P-dichlorophosphoryloxy)phenyl]phosphine oxide (hereinafter referred to as "DCPPP") was quantitatively obtained.

Then, the total amount of the product obtained in the foregoing step (DCPPP) was loaded into the same four-necked flask as that described above. 100 ml of THF were added to the flask, and the mixture was placed under nitrogen. While the mixture was stirred at 0 to 5° C., a solution prepared by dissolving 48.59 g (500 mmol) of diallylamine and 50.5 g (500 mmol) of TEA in 100 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the remainder was condensed under reduced pressure so as to be a solution in chloroform. The resultant was washed with water, dried with anhydrous sodium sulfate, filtrated, and dried and solidified under reduced pressure, whereby 46.3 g of a target compound were obtained (in 86% yield).

The results of the infrared absorption spectrometry, NMR, and TOF-mass spectrometry of the compound were as described below, and the structure of Compound (II-3) shown above was identified.

Infrared absorption spectrometry (cm$^{-1}$): $v_{(CH2=CH)}$ 1625, $v_{(ring)}$ 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (12H), allyl C—H 3.4-4.1, 5.1-6.1 (60H)

TOF-mass spectrometry (M/Z): 1043, 1044, 1045 (calculated molecular weight=1041.2)

Example 10

Synthesis of Compound (II-4)

33.6 g of a target compound were obtained (in 84% yield) in the same manner as in Example 9 except that 28.6 g (500 mmol) of allylamine were used instead of diallylamine.

The results of the infrared absorption spectrometry, NMR, and TOF-mass spectrometry of the compound were as described below, and the structure of Compound (II-4) shown above was identified.

Infrared absorption spectrometry (cm$^{-1}$): $v_{(NH)}$ 3280, 1640, $v_{(CH2=CH)}$ 1625, $v_{(ring)}$ 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (12H), N—H 4.7 (6H), allyl C—H 3.2-4.3, 5.0-6.1 (30H)

TOF-mass spectrometry (M/Z): 802, 803, 804 (calculated molecular weight=800.2)

Example 11

Synthesis of Compound (II-5)

37.9 g of a target compound were obtained (in 94% yield) in the same manner as in Example 9 except that 29.0 g (500 mmol) of allyl alcohol were used instead of diallylamine.

The results of the infrared absorption spectrometry, NMR, and TOF-mass spectrometry of the compound were as described below, and the structure of Compound (II-5) shown above was identified.

Infrared absorption spectrometry (cm$^{-1}$): $v_{(CH2=CH)}$ 1625, $v_{(ring)}$ 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (12H), allyl C—H 3.4-4.0, 5.1-6.1 (30H)

TOF-mass spectrometry (M/Z): 808, 809, 811 (calculated molecular weight=806.7)

Example 12

Synthesis of Compound (II-6)

33.0 g of a target compound were obtained (in 93% yield) in the same manner as in Example 9 except that 100 ml of a solution of 50.4 g (500 mmol) of allyl magnesium chloride in THF were used instead of diallylamine.

The results of the infrared absorption spectrometry, NMR, and TOF-mass spectrometry of the compound were as described below, and the structure of Compound (II-6) shown above was identified.

Infrared absorption spectrometry (cm$^{-1}$): $v_{(CH2=CH)}$ 1625, $v_{(ring)}$ 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (12H), allyl C—H 3.5-4.0, 5.2-6.0 (30H)

TOF-mass spectrometry (M/Z): 712, 713, 714 (calculated molecular weight=710.5)

Example 13

Synthesis of Compound (II-7)

153.2 g (1.00 mol) of phosphorus oxychloride and 100 ml of THF were loaded into a 300-ml four-necked flask equipped with the same devices as those of Example 7. The mixture was placed under nitrogen, and was stirred at 0 to 5° C. During the stirring, the mixed liquid of 48.6 g (500 mmol) of diallylamine and 50.5 g (500 mmol) of TEA was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive phosphorus oxychloride were removed by distillation under reduced pressure. The residue was distilled under reduced pressure so that a fraction at 98 to 101° C./5 mmHg was collected. Thus, 78.1 g of dichlorophosphoryl(N,N-diallyl) amide (hereinafter referred to as "DCPA") were obtained (in 73% yield).

64.2 g (300 mmol) of DCPA and 100 ml of THF were loaded into the same four-necked flask as that described above. The mixture was placed under nitrogen, and was stirred at 0 to 5° C. During the stirring, a solution prepared by dissolving 16.3 g (50.0 mmol) of HPP (see Example 9) and 30.3 (300 mmol) of TEA in 100 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive DCPA were removed by distillation under reduced pressure. The total amount of the residue was returned to the above-mentioned device, and 100 ml of THF were added to dissolve the residue. Next, the solution was placed under nitrogen, and was stirred at 0 to 5° C. During the stirring, a solution prepared by dissolving 34.3 g (600 mmol) of allylamine and 30.3 g (300 mmol) of TEA in 100 ml of THF was slowly added to the mixture from the dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 40.1 g of a target compound were obtained (in 87% yield).

The results of the infrared absorption spectrometry, NMR, and TOF-mass spectrometry of the compound were as described below, and the structure of Compound (II-7) shown above was identified.

Infrared absorption spectrometry (cm$^{-1}$): $v_{(NH)}$ 3280, 1640, $v_{(CH2=CH)}$ 1625, $v_{(ring)}$ 1594, 1495, $v_{(P=O)}$ 1200-1300, $v_{(P-O-C)}$ 1210, 980 ($v_{(OH)}$3200 disappeared)

$^1$H-NMR spectrometry (δ, ppm): phenyl C—H 7.0-7.5 (12H), N—H 4.7 (3H), allyl C—H 3.4-4.2, 5.0-6.0 (45H)

TOF-mass spectrometry (M/Z): 923, 924, 925 (calculated molecular weight=921.0)

Example 14

Synthesis of Compound (II-8)

12.2 g (500 mmol) of metal magnesium and 250 ml of diethyl ether were loaded into a 500-ml four-necked flask equipped with the same devices as those of Example 7. The mixture was placed under nitrogen, and a small amount of iodine was added to activate the mixture. 63.3 g (500 mmol) of benzyl chloride were slowly added to the resultant from a dropping funnel in order that a mild boiling point reflux state might be maintained. After the completion of the dropping, the resultant was subjected to a reaction under boiling point reflux for 3 hours and then at room temperature for 3 hours. During the period, the total amount of metal magnesium reacted, whereby a benzylmagnesium chloride solution was quantitatively obtained.

Next, 153.3 g (1.00 mol) of phosphorus oxychloride and 100 ml of diethyl ether were loaded into the same four-necked flask as that described above. The mixture was placed under nitrogen, and was stirred at 0 to 5° C. During the stirring, the total amount of the benzylmagnesium chloride solution obtained in the foregoing step was slowly added to the mixture from a dropping funnel. After the completion of the dropping, the resultant was subjected to a reaction at the temperature for 6 hours and then at room temperature for 24 hours. After that, a magnesium salt was removed by filtration, and then the solvent and excessive phosphorus oxychloride were removed by distillation under reduced pressure. The residue was distilled under reduced pressure so that a fraction at 99 to 102° C./5 mmHg was collected. Thus, 81.5 g of benzylphosphonic dichloride (hereinafter referred to as "BzPDC") were obtained (in 78% yield) It should be noted that TOF-mass spectrometry confirmed that the compound was BzPDC.

TOF-mass spectrometry (M/Z): 211, 212, 213 (calculated molecular weight=209.0)

Next, 52.3 g (250 mmol) of BzPDC and 150 ml of THF were loaded into the same four-necked flask as that described above. The mixture was placed under nitrogen, and was stirred at 0 to 5° C. During the stirring, a solution prepared by dissolving 24.3 g (250 mmol) of diallylamine and 50.5 g (500 mmol) of TEA in 150 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive amine were removed by distillation under reduced pressure. The residue was distilled under reduced pressure so that a fraction at 128 to 133° C./4 mmHg was collected. Thus, 51.3 g of benzylphosphonic mono(N,N-diallyl) amide monochloride (hereinafter referred to as "BzPAC") were obtained (in 76% yield). It should be noted that TOF-mass spectrometry confirmed that the compound was BzPAC.

TOF-mass spectrometry (M/Z): 271, 272, 273 (calculated molecular weight=269.8)

Next, 16.3 g (50.0 mmol) of HPP (see Example 9) and 100 ml of DMF were loaded into the same four-necked flask as that described above. The mixture was placed under nitrogen, and was stirred at 0 to 5° C. During the stirring, a solution prepared by dissolving 40.5 g (150 mmol) of BzPAC and 30.3 g (300 mmol) of TEA in 100 ml of DMF was slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 35.2 g of a target compound were obtained (in 91% yield).

The results of the infrared absorption spectrometry, NMR, and TOF-mass spectrometry of the compound were as described below, and the structure of Compound (II-8) shown above was identified.

Infrared absorption spectrometry (cm$^{-1}$): $v_{(CH2=CH)}$ 1625, $v_{(ring)}$ 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): phenyl C—H 7.0-7.5 (27H), benzyl-CH$_2$— 4.7 (6H), allyl C—H 3.4-4.2, 5.0-6.0 (30H)

TOF-mass spectrometry (M/Z): 1028, 1029, 1030 (calculated molecular weight=1026.0)

Example 15

Synthesis of Compound (II-9)

12.2 g (500 mmol) of metal magnesium and 150 ml of diethyl ether were loaded into a 500-ml four-necked flask equipped with the same devices as those of Example 7. The mixture was placed under nitrogen, and a small amount of iodine was added to activate the mixture. 300 ml of a solution of 103.1 g (500 mmol) of α-bromonaphthalene in diethyl ether were slowly added to the resultant from a dropping funnel in order that a mild boiling point reflux state might be maintained. After the completion of the dropping, the resultant was subjected to a reaction under boiling point reflux for 6 hours and then at room temperature for 6 hours. During the period, the total amount of metal magnesium reacted, whereby an α-naphthylmagnesium bromide solution was quantitatively obtained.

Then, 153.3 g (1.00 mol) of phosphorus oxychloride and 100 ml of diethyl ether were loaded into a 1,000-ml four-necked flask equipped with the same devices as those described above. The mixture was placed under nitrogen, and was stirred at 0 to 5° C. During the stirring, the total amount of the α-naphthylmagnesium bromide solution obtained in the foregoing step was slowly added to the mixture from a dropping funnel. After the completion of the dropping, the resultant was subjected to a reaction at the temperature for 6 hours and then at room temperature for 24 hours. After that, a magnesium salt was removed by filtration, and then the solvent and excessive phosphorus oxychloride were removed by distillation under reduced pressure, whereby 117.6 g of α-naphthylphosphonicdichloride (hereinafter referred to as "αNPDC") were obtained (in 96% yield). It should be noted that TOF-mass spectrometry confirmed that the above-mentioned compound was αNPDC.

TOF-mass spectrometry (M/Z): 256, 257, 258 (calculated molecular weight=254.0)

Next, 61.3 g (250 mmol) of αNPDC and 150 ml of THF were loaded into a 500-ml four-necked flask equipped with the same devices as those described above. The mixture was placed under nitrogen, and was stirred at 0 to 5° C. During the stirring, 200 ml of a solution of 50.4 g (500 mmol) of allyl magnesium chloride in THF were slowly added to the mixture from a dropping funnel. After the completion of the dropping, the resultant was subjected to a reaction at the temperature for 6 hours and then at room temperature for 24 hours. After that, an amine salt was removed by filtration, and then the solvent was removed by distillation under reduced pressure. The residue was distilled under reduced pressure so that a fraction at 158 to 162° C./4 mmHg was collected. Thus, 66.7 g of P-allyl, P-(α-naphthyl) phosphonic chloride (hereinafter referred to as "AαNPC") were obtained (in 84% yield). It should be noted that TOF-mass spectrometry confirmed that the compound was AαNPC.

TOF-mass spectrometry (M/Z): 253, 254, 255 (calculated molecular weight=250.7)

Next, 16.3 g (50.0 mmol) of HPP (see Example 9), 30.3 (300 mmol) of TEA, and 100 ml of DMF were loaded into a 300-ml four-necked flask equipped with the same devices as those described above. The mixture was placed under nitrogen, and was stirred at 0 to 5° C. During the stirring, 150 ml of a solution of 37.6 g (150 mmol) of AαNPC in DMF were slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 46.6 g of a target compound were obtained (in 91% yield).

The results of the infrared absorption spectrometry, NMR, and TOF-mass spectrometry of the compound were as described below, and the structure of Compound (II-9) shown above was identified.

Infrared absorption spectrometry (cm$^{-1}$): $v_{(CH2=CH)}$ 1625, $v_{(ring)}$ 1603, 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): aromatic C—H 6.8-7.5 (33H), allyl C—H 3.4-4.2, 5.0-6.1 (15H)

TOF-mass spectrometry (M/Z): 970, 971, 972 (calculated molecular weight=968.9)

Example 16

Synthesis of Compound (II-10)

116.5 g of β-naphthylphosphonic dichloride (hereinafter referred to as "βNPDC") were obtained (in 95% yield) in the same manner as in Example 15 except that 103.1 g (500 mmol) of β-bromonaphthalene were used instead of α-bromonaphthalene. It should be noted that TOF-mass spectrometry confirmed that the compound was βNPDC.

TOF-mass spectrometry (M/Z): 256, 257, 258 (calculated molecular weight=254.0)

Next, 61.3 g (250 mmol) of βNPDC and 150 ml of THF were loaded into the same four-necked flask as that described above. The mixture was placed under nitrogen, and was stirred at 0 to 5° C. During the stirring, a solution prepared by dissolving 28.6 g (500 mmol) of allylamine and 101 g (1.00 mol) of TEA in 200 ml of THF was slowly added to the mixture from a dropping funnel. After the completion of the dropping, the resultant was subjected to a reaction at the temperature for 6 hours and then at room temperature for 24 hours. After that, a magnesium salt was removed by filtration, and then the solvent was removed by distillation under reduced pressure. The residue was distilled under reduced pressure so that a fraction at 168 to 170° C./4 mmHg was collected. Thus, 97.9 g of β-naphthylphosphonicmono(N-allyl)amide monochloride (hereinafter referred to as "βNPAC") were obtained (in 74% yield). It should be noted that TOF-mass spectrometry confirmed that the compound was βNPAC.

TOF-mass spectrometry (M/Z): 266, 267, 268 (calculated molecular weight=264.5)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, 150 ml of a solution of 39.7 g (150 mmol) of βNPAC in DMF were slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 50.0 g of a target compound were obtained (in 92% yield).

The results of the infrared absorption spectrometry, NMR, and TOF-mass spectrometry of the compound were as described below, and the structure of Compound (II-10) shown above was identified.

Infrared absorption spectrometry (cm$^{-1}$): $v_{(NH)}$ 3320, 1640, $v_{(CH2=CH)}$ 1625, $v_{(ring)}$ 1600, 1495, $v_{(P=O)}$ 1200-1300, $v_{(P-O-C)}$ 1210, 980 ($v_{(OH)}$ 3200 disappeared)

$^1$H-NMR spectrometry (δ, ppm): aromatic C—H 6.9-7.5 (33H), N—H 4.8 (3H), allyl C—H 3.4-4.2, 5.0-6.1 (15H)

TOF-mass spectrometry (M/Z): 1015, 1016, 1017 (calculated molecular weight=1013.95)

Example 17

Synthesis of Compound (II-11)

12.2 g (500 mmol) of metal magnesium and 250 ml of diethyl ether were loaded into a 500-ml four-necked flask equipped with the same devices as those of Example 7. The mixture was placed under nitrogen, and a small amount of iodine was added to activate the mixture. A solution prepared by dissolving 116.1 g (500 mmol) of 4-bromobiphenyl in 150 ml of diethyl ether was slowly added to the resultant from a dropping funnel in order that a mild boiling point reflux state might be maintained. After the completion of the dropping, the resultant was subjected to a reaction under boiling point reflux for 3 hours and then at room temperature for 3 hours. During the period, the total amount of metal magnesium reacted, whereby a 4-biphenylmagnesium bromide solution was quantitatively obtained.

Next, 153.3 g (1.00 mol) of phosphorus oxychloride and 100 ml of diethyl ether were loaded into the same four-necked flask as that described above. The mixture was placed under nitrogen, and was stirred at 0 to 5° C. During the stirring, the total amount of the 4-biphenylmagnesium chloride solution obtained in the foregoing step was slowly added to the mixture from a dropping funnel. After the completion of the dropping, the resultant was subjected to a reaction at the temperature for 6 hours and then at room temperature for 24 hours. After that, a magnesium salt was removed by filtration, and then the solvent and excessive phosphorus oxychloride were removed by distillation under reduced pressure. The residue was recrystallized from a petroleum ether/benzene mixed solvent, whereby 97.6 g of 4-biphenylphosphonic dichloride
(hereinafter referred to as "BPPDC") as a white, needle-like crystal were obtained (in 72% yield). It should be noted that TOF-mass spectrometry confirmed that the white, needle-like crystal was BPPDC.

TOF-mass spectrometry (M/Z): 273, 274, 275 (calculated molecular weight=271.1)

Then, 67.8 g (250 mmol) of BPPDC and 150 ml of THF were loaded into the same four-necked flask as that described above. 100 ml of a solution of 25.2 g (250 mmol) of allyl magnesium chloride in THF were slowly added to the mixture from a dropping funnel. After the completion of the dropping, the resultant was subjected to a reaction at the temperature for 6 hours and then at room temperature for 24 hours. After that, a magnesium salt was removed by filtration, and then the solvent was removed by distillation under reduced pressure. The remainder was recrystallized from a petroleum ether/benzene mixed solvent, whereby 59.5 g of P-allyl, P-(4-biphenyl) phosphonic chloride (hereinafter referred to as "ABPC") as a white, needle-like crystal were obtained (in 86% yield). It should be noted that TOF-mass spectrometry confirmed that the compound was ABPC.

TOF-mass spectrometry (M/Z): 268, 269, 270 (calculated molecular weight=276.7)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, 150 ml of a solution of 41.5 g (150 mmol) of ABPC in DMF were slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 46.6 g of a target compound were obtained (in 91% yield).

The results of the infrared absorption spectrometry, NMR, and TOF-mass spectrometry of the compound were as described below, and the structure of Compound (II-11) shown above was identified.

Infrared absorption spectrometry (cm$^{-1}$): $v_{(CH2=CH)}$ 1625, $v_{(ring)}$ 1603, 1594, 1495, $v_{(P=O)}$ 1200-1300, $v_{(P-O-C)}$ 1210, 980 ($v_{(OH)}$ 3200 disappeared)

$^1$H-NMR spectrometry (δ, ppm): aromatic C—H 7.0-7.5 (39H), allyl C—H 3.3-4.2, 5.0-6.1 (15H)

TOF-mass spectrometry (M/Z): 1049, 1050, 1051 (calculated molecular weight=1047.1)

Example 18

Synthesis of Compound (II-12)

105.5 g (500 mmol) of phenylphosphoric dichloride and 150 ml of THF were loaded into a 500-ml four-necked flask equipped with the same devices as those of Example 7. The mixture was placed under nitrogen, and was stirred at 0 to 5° C. During the stirring, a solution prepared by dissolving 48.6 g (500 mmol) of diallylamine and 101 g (1.00 mol) of TEA in 150 ml of THF was slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by filtration under reduced pressure. The residue was distilled under reduced pressure so that a fraction at 122 to 126° C./5 mmHg was collected. Thus, 116.8 g of phenylphosphoric mono(N,N-diallyl)amide monochloride (hereinafter referred to as "POPAC") were obtained (in 86% yield). It should be noted that TOF-mass spectrometry confirmed that the compound was POPAC.

TOF-mass spectrometry (M/Z): 273, 274, 275 (calculated molecular weight=271.1)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, 150 ml of a solution of 40.8 g (150 mmol) of POPAC in DMF were slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by filtration under reduced pressure. The residue was dissolved in chloroform, and the resultant was washed with water, dried with anhydrous sodium sulfate, filtrated, and dried and solidified under reduced pressure, whereby 46.6 g of a target compound were obtained (in 91% yield).

The results of the infrared absorption spectrometry, NMR, and TOF-mass spectrometry of the compound were as described below, and the structure of Compound (II-12) shown above was identified.

Infrared absorption spectrometry (cm$^{-1}$): $v_{(CH2=CH)}$ 1625, $v_{(ring)}$ 1600, 1595, 1495, $v_{(P=O)}$ 1200-1300, $v_{(P-O-C)}$ 1210, 980

$^1$H-NMR spectrometry (δ, ppm): aromatic C—H 7.0-7.5 (27H), allyl C—H 3.3-4.2, 5.0-6.1 (30H)

TOF-mass spectrometry (M/Z): 1034, 1035, 1036 (calculated molecular weight=1032.0)

Example 19

Synthesis of Compound (II-13)

230.0 g (1.50 mol) of phosphorus oxychloride and 150 ml of THF were loaded into a 500-ml four-necked flask equipped with the same devices as those of Example 7. The mixture was placed under nitrogen, and was stirred at 0 to 5° C. During the stirring, a solution prepared by dissolving 108.2 g (1.00 mol) of benzyl alcohol and 152 g (1.50 mol) of TEA in 200 ml of THF was slowly added to the mixture from a dropping funnel. After the completion of the dropping, the resultant was subjected to a reaction at the temperature for 6 hours and then at room temperature for 24 hours. After the produced amine salt had been removed by filtration, excessive phosphorus oxychloride, TEA, and the solvent were removed by distillation under reduced pressure, whereby 207.0 g of benzylphosphoric dichloride (hereinafter referred to as "BzOPDC") were obtained (in 92% yield). It should be noted that TOF-mass spectrometry confirmed that the compound was BzOPDC.

TOF-mass spectrometry (M/Z): 227, 228, 229 (calculated molecular weight=225.0)

Next, 112.5 g (500 mmol) of BzOPDC and 150 ml of THF were loaded into a 500-ml four-necked flask equipped with the same devices as those described above. The mixture was placed under nitrogen, and was stirred at 0 to 5° C. During the stirring, a solution prepared by dissolving 48.6 g (500 mmol) of diallylamine and 101 g (1.00 mol) of TEA in 150 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive amine were distilled under reduced pressure so that 125.7 g of benzylphosphoric mono(N,N-diallyl)amide monochloride (hereinafter referred to as "BzOPAC") were obtained as the residue (in 88% yield). It should be noted that TOF-mass spectrometry confirmed that the compound was BzOPAC.

TOF-mass spectrometry (M/Z): 287, 288, 289 (calculated molecular weight=285.7)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, 150 ml of a solution of 42.9 g (150 mmol) of BzOPAC in DMF were slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 46.6 g of a target compound were obtained (in 91% yield).

The results of the infrared absorption spectrometry, NMR, and TOF-mass spectrometry of the compound were as described below, and the structure of Compound (II-13) shown above was identified.

Infrared absorption spectrometry (cm$^{-1}$): $v_{(CH2=CH)}$ 1625, $v_{(ring)}$ 1603, 1594, 1495, $v_{(P=O)}$ 1200-1300, $v_{(P—O—C)}$ 1210, 980

$^1$H-NMR spectrometry (δ, ppm): aromatic C—H 6.9-7.5 (27H), benzyl-CH$_2$— 4.4 (6H), allyl C—H 3.3-4.2, 5.0-6.2 (30H)

TOF-mass spectrometry (M/Z): 1076, 1077, 1078 (calculated molecular weight=1074.1)

Example 20

Synthesis of Compound (II-14)

230.0 g (1.50 mol) of phosphorus oxychloride and 150 ml of THF were loaded into a 500-ml four-necked flask equipped with the same devices as those of Example 7. The mixture was placed under nitrogen, and was stirred at 0 to 5° C. During the stirring, a solution prepared by dissolving 144.2 g (1.00 mol) of α-naphthol and 152 g (1.50 mol) of TEA in 200 ml of THF was slowly added to the mixture from a dropping funnel. After the completion of the dropping, the resultant was subjected to a reaction at the temperature for 6 hours and then at room temperature for 24 hours. After the produced amine salt had been removed by filtration, excessive phosphorus oxychloride, TEA, and the solvent were removed by distillation under reduced pressure, whereby 245.3 g of α-naphthylphosphoricdichloride (hereinafter referred to as "αNOPDC") were obtained (in 94% yield). It should be noted that TOF-mass spectrometry confirmed that the compound was αNOPDC.

TOF-mass spectrometry (M/Z): 263, 264, 265 (calculated molecular weight=261.0)

Next, 130.5 g (500 mmol) of αNOPDC and 150 ml of THF were loaded into the same four-necked flask as that described above. The mixture was placed under nitrogen, and was stirred at 0 to 5° C. During the stirring, a solution prepared by dissolving 48.6 g (500 mmol) of diallylamine and 101 g (1.00 mol) of TEA in 150 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive amine were removed by distillation under reduced pressure. Thus, 146.4 g of α-naphthylphosphoric mono(N,N-diallyl)amide monochloride (hereinafter referred to as "αNOPAC") were obtained as the residue (in 91% yield). It should be noted that TOF-mass spectrometry confirmed that the compound was αNOPAC.

TOF-mass spectrometry (M/Z): 323, 324, 325 (calculated molecular weight=321.8)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, a solution prepared by dissolving 48.3 g (150 mmol) of αNOPAC in 150 ml of DMF was slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 52.6 g of a target compound were obtained (in 89% yield).

The results of the infrared absorption spectrometry, NMR, and TOF-mass spectrometry of the compound were as described below, and the structure of Compound (II-14) shown above was identified.

Infrared absorption spectrometry (cm$^{-1}$): $v_{(CH2=CH)}$ 1625, $v_{(ring)}$ 1604, 1595, 1495, $v_{(P=O)}$ 1200-1300, $v_{(P-O-C)}$ 1210, 980

1H-NMR spectrometry (δ, ppm): aromatic C—H 7.0-7.6 (33H), allyl C—H 3.3-4.2, 5.0-6.1 (30H)

TOF-mass spectrometry (M/Z): 1184, 1185, 1186 (calculated molecular weight=1182.2)

Example 21

Synthesis of Compound (II-15)

230.0 g (1.50 mol) of phosphorus oxychloride and 150 ml of THF were loaded into a 500-ml four-necked flask equipped with the same devices as those of Example 7. The mixture was placed under nitrogen, and was stirred at 0 to 5° C. During the stirring, a solution prepared by dissolving 144.2 g (1.00 mol) of β-naphthol and 152 g (1.50 mol) of TEA in 200 ml of THF was slowly added to the mixture from a dropping funnel. After the completion of the dropping, the resultant was subjected to a reaction at the temperature for 6 hours and then at room temperature for 24 hours. After the produced amine salt had been removed by filtration, excessive phosphorus oxychloride, TEA, and the solvent were removed by distillation under reduced pressure, whereby 237.5 g of β-naphthylphosphoricdichloride (hereinafter referred to as "βNOPDC") were obtained (in 91% yield). It should be noted that TOF-mass spectrometry confirmed that the compound was βNOPDC.

TOF-mass spectrometry (M/Z): 263, 264, 265 (calculated molecular weight=261.0)

Next, 130.5 g (500 mmol) of βNOPDC and 150 ml of THF were loaded into the same four-necked flask as that described above. The mixture was placed under nitrogen, and was stirred at 0 to 5° C. During the stirring, a solution prepared by dissolving 48.6 g (500 mmol) of diallylamine and 101 g (1.00 mol) of TEA in 150 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive amine were removed by distillation under reduced pressure. Thus, 144.8 g of β-naphthylphosphoric mono(N,N-diallyl)amide monochloride (hereinafter referred to as "βNOPAC") were obtained as the residue (in 90% yield). It should be noted that TOF-mass spectrometry confirmed that the compound was βNOPAC.

TOF-mass spectrometry (M/Z): 323, 324, 325 (calculated molecular weight=321.8)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, a solution prepared by dissolving 48.3 g (150 mmol) of βNOPAC in 150 ml of DMF was slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 53.8 g of a target compound were obtained (in 91% yield).

The results of the infrared absorption spectrometry, NMR, and TOF-mass spectrometry of the compound were as described below, and the structure of Compound (II-15) shown above was identified.

Infrared absorption spectrometry (cm$^{-1}$): $v_{(CH2=CH)}$ 1625, $v_{(ring)}$ 1600, 1594, 1495, $v_{(P=O)}$ 1200-1300, $v_{(P-O-C)}$ 1210, 980

$^1$H-NMR spectrometry (δ, ppm): aromatic C—H 6.9-7.5 (33H), allyl C—H 3.3-4.2, 5.0-6.2 (30H)

TOF-mass spectrometry (M/Z): 1184, 1185, 1186 (calculated molecular weight=1182.2)

Example 22

Synthesis of Compound (II-16)

230.0 g (1.50 mol) of phosphorus oxychloride and 150 ml of THF were loaded into a 500-ml four-necked flask equipped with the same devices as those of Example 7. The mixture was placed under nitrogen, and was stirred at 0 to 5° C. During the stirring, a solution prepared by dissolving 170.2 g (1.00 mol) of 4-biphenyl alcohol and 152 g (1.50 mol) of TEA in 200 ml of THF was slowly added to the mixture from a dropping funnel. After the completion of the dropping, the resultant was subjected to a reaction at the temperature for 6 hours and then at room temperature for 24 hours. After the produced amine salt had been removed by filtration, excessive phosphorus oxychloride, TEA, and the solvent were removed by distillation under reduced pressure, whereby 267.0 g of 4-biphenylphosphoric dichloride (hereinafter referred to as "BPOPDC") were obtained (in 93% yield). It should be noted that TOF-mass spectrometry confirmed that the compound was BPOPDC.

TOF-mass spectrometry (M/Z): 289, 290, 291 (calculated molecular weight=287.1)

Next, 143.6 g (500 mmol) of BPOPDC and 150 ml of THF were loaded into the same four-necked flask as that described above. The mixture was placed under nitrogen, and was stirred at 0 to 5° C. During the stirring, a solution prepared by dissolving 48.6 g (500 mmol) of diallylamine and 101 g (1.00 mol) of TEA in 150 ml of THF was slowly added to the mixture from a dropping funnel. After the completion of the dropping, the resultant was subjected to a reaction at the temperature for 6 hours and then at room temperature for 24 hours. After that, an amine salt was removed by filtration, and then the solvent and excessive amine were removed by distillation under reduced pressure. Thus, 156.5 g of 4-biphenylphosphoric mono(N,N-diallyl)amide monochloride (hereinafter referred to as "BPOPAC") were obtained as the residue (in 90% yield). It should be noted that TOF-mass spectrometry confirmed that the compound was BPOPAC.

TOF-mass spectrometry (M/Z): 349, 350, 351 (calculated molecular weight=347.8)

Next, 16.3 g (50.0 mmol) of HPP (see Example 9), 30.3 g (300 mmol) of TEA, and 100 ml of DMF were loaded into the same four-necked flask as that described above. The mixture was placed under nitrogen, and was stirred at 0 to 5° C. During the stirring, 150 ml of a solution of 52.2 g (150 mmol) of BPOPAC in DMF was slowly added to the mixture from a dropping funnel. After the completion of the dropping, the resultant was subjected to a reaction at the temperature for 6 hours and then at room temperature for 24 hours. After an amine salt had been removed by filtration, the solvent and excessive amine were removed by distillation under reduced pressure. The residue was dissolved in chloroform, and the resultant was washed with water, dried with anhydrous sodium sulfate, filtrated, and dried and solidified under reduced pressure, whereby 57.3 g of a target compound were obtained (in 91% yield).

The results of the infrared absorption spectrometry, NMR, and TOF-mass spectrometry of the compound were as described below, and the structure of Compound (II-16) shown above was identified.

Infrared absorption spectrometry (cm$^{-1}$): $v_{(CH2=CH)}$ 1625, $v_{(ring)}$ 1603, 1594, 1495, $v_{(P=O)}$ 1200-1300, $v_{(P-O-C)}$ 1210, 980

$^1$H-NMR spectrometry (δ, ppm): aromatic C—H 6.8-7.5 (39H), allyl C—H 3.3-4.2, 5.0-6.1 (30H)

TOF-mass spectrometry (M/Z): 1262, 1263, 1264 (calculated molecular weight=1260.3)

Example 23

Synthesis of Compound (II-17)

22.3 g (50.0 mmol) of AHP (see Example 7), 20.2 g (200 mmol) of TEA, and 100 ml of distilled DMF were loaded into the same four-necked flask as that of Example 7. The mixture was placed under nitrogen, and was stirred at 0 to 5° C. During the stirring, under nitrogen, a solution prepared by dissolving 40.3 g (150 mmol) of diphenylphosphoric chloride in 150 ml of DMF was slowly added to the mixture from a dropping funnel. After the completion of the dropping, the resultant was subjected to a reaction at the temperature for 3 hours, then at room temperature for 6 hours, and then at 80° C. for 24 hours. After that, the resultant was dried and solidified under reduced pressure, and was then dissolved in chloroform. The resultant was washed with water, and a chloroform phase was dehydrated with anhydrous sodium sulfate, filtrated, and dried and solidified under reduced pressure, whereby 52.6 g of a target compound were obtained (in 92% yield).

The results of the infrared absorption spectrometry, NMR, and TOF-mass spectrometry of the compound were as described below, and the structure of Compound (II-17) shown above was identified.

Infrared absorption spectrometry (cm$^{-1}$): $v_{(CH2=CH)}$ 1625, $v_{(ring)}$ 1602, 1495, $v_{(P=O)}$ 1200-1300, $v_{(P-O-C)}$ 1210, 980, ($v_{(OH)}$ 3200 disappeared)

$^1$H-NMR spectrometry (δ, ppm): phenyl C—H 7.0-7.5 (39H), allyl C—H 3.4-4.1, 5.1-6.1 (15H)

TOF-mass spectrometry (M/Z): 1144, 1145, 1146 (calculated molecular weight=1142.99)

<Test of Flame Retardant for Physical Properties>

Test Example 1

The thermogravimetric curve (TG curve) of each of the following organophosphorus compounds was determined with a TG/DTA 6200 (manufactured by Seiko Instruments Inc.) by increasing the temperature of each of the compounds under conditions including a sample amount of 5 mg and a rate of temperature increase of 10° C./min. In addition, the ratio at which a carbide was produced under a nitrogen atmosphere at 600° C. was measured. FIG. 1 shows the TG curve of each of the following organophosphorus compounds, and Table 1 shows the ratio at which a carbide is produced of each of the compounds.

TABLE 1

[Chem 22]

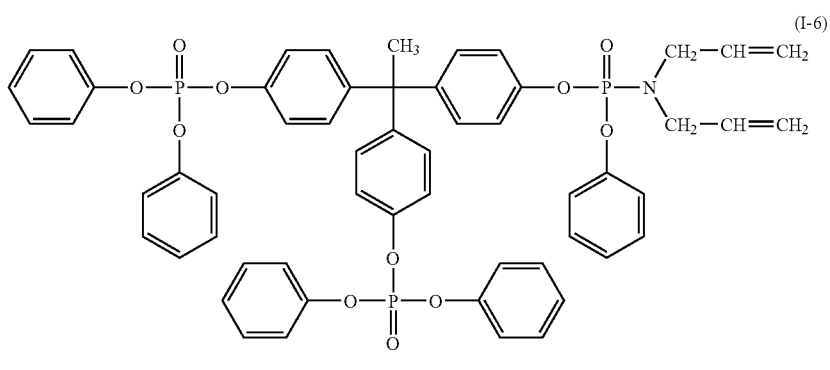

(I-6)

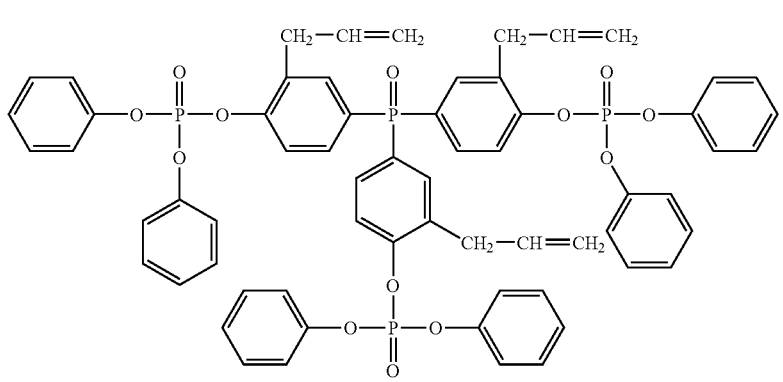

(II-17)

TABLE 1-continued (III-1)

[Chemical structure of Compound (III-1): a phosphate with three aryl groups bearing CH₂-CH=CH₂ (allyl) substituents]

|  | Compound (I-6) | Compound (II-17) | Compound (III-1) |
|---|---|---|---|
| Phosporus content | 9.24 | 11.00 | 6.95 |
| Ratio at which carbide is produced | 31.30 | 33.00 | 2.10 |

*[1]Production ratio under a nitrogen atmosphere at 600° C.

As is apparent from the above-mentioned test results, the organophosphorus compound of the present invention [Compound (1-6) or Compound (II-17)] has a heat decomposition temperature higher than that of a conventional organophosphorus compound [Compound (III-1)], and is more energetically stable than the conventional organophosphorus compound, so its flame retardant component hardly vaporizes upon molding, and a resin processed article has excellent moldability or pocessability. In addition, the organophosphorus compound of the present invention has a high phosphorus content, and shows a high ratio at which a carbide is produced, so a char (pyrolysis residue) exhibiting an extremely large shielding action on heat or oxygen can be easily formed, and high flame retardance can be exerted.

<Production of Flame-Retardant Resin Processed Article>

Example 24

47.3 parts by mass of a 6/66 nylon copolymer (manufactured by UBE INDUSTRIES, LTD.: 2123B) as a thermoplastic resin, 30 parts by mass of glass fibers each having a surface treated with a silane coupling agent and each having a fiber length of about 3 mm (manufactured by ASAHI FIBER GLASS Co., Ltd.: 03.JAFT2Ak25) as reinforced fibers, 0.5 part by mass of carbon black as a colorant, 0.2 part by mass of an antioxidant (manufactured by Ciba-Geigy: IRGANOX 1010), 6 parts by mass of talc having a particle diameter of 2 μm (manufactured by Nippon Talc Co., Ltd.) and 5 parts by mass of clay having a nano particle diameter (manufactured by Nissho Iwai Bentonite: NANOMER 1.30T) as inorganic fillers, and 11 parts by mass of a reactive flame retardant represented by the above formula (I-4) as a flame retardant were blended with one another, and the whole was kneaded with a side flow type biaxial extruder (manufactured by The Japan Steel Works, LTD.) at 280° C., whereby a resin pellet was obtained. After having been dried at 105° C. for 4 hours, the above-mentioned resin pellet was molded with an injection molding machine (manufactured by FUNUC: α50C) under conditions including a resin temperature of 280° C. and a mold temperature of 80° C.

After that, the above-mentioned molded article was irradiated with γ-rays at a dose of 25 kGy by using cobalt 60 as a radiation source, whereby a resin processed article of Example 24 was obtained.

Example 25

51.3 parts by mass of a 66 nylon copolymer (manufactured by UBE INDUSTRIES, LTD.: 2020B) as a thermoplastic resin, 25 parts by mass of glass fibers each having a surface treated with a silane coupling agent and each having a fiber length of about 3 mm (manufactured by ASAHI FIBER GLASS Co., Ltd.: 03.JAFT2Ak25) as reinforced fibers, 0.5 part by mass of carbon black as a colorant, 0.2 part by mass of an antioxidant (manufactured by Ciba-Geigy: IRGANOX 1010), 6 parts by mass of talc having a particle diameter of 2 μm (manufactured by Nippon Talc Co., Ltd.) and 5 parts by mass of clay having a nano particle diameter (manufactured by Nissho Iwai Bentonite: NANOMER 1.30T) as inorganic fillers, and 12 parts by mass of a reactive flame retardant represented by the above formula (I-3) as a flame retardant were blended with one another, and the whole was kneaded with a side flow type biaxial extruder (manufactured by The Japan Steel Works, LTD.) at 280° C., whereby a resin pellet was obtained. After having been dried at 105° C. for 4 hours, the above-mentioned resin pellet was molded with an injection molding machine (manufactured by FUNUC: α50C) under conditions including a resin temperature of 280° C. and a mold temperature of 80° C.

After that, the above-mentioned molded article was irradiated with γ-rays at a dose of 25 kGy by using cobalt 60 as a radiation source, whereby a resin processed article of Example 25 was obtained.

Example 26

45.3 parts by mass of 66 nylon (manufactured by UBE INDUSTRIES, LTD.: 2020B) as a thermoplastic resin, 10 parts by mass of talc having a particle diameter of 2 μm (manufactured by Nippon Talc Co., Ltd.) and 5 parts by mass of clay having a nano particle diameter (manufactured by Nissho Iwai Bentonite: NANOMER 1.30T) as inorganic fillers, 0.5 part by mass of carbon black as a colorant, 8 parts by mass of a reactive flame retardant represented by the above formula (I-3) and 6 parts by mass of a reactive flame retardant represented by the above formula (I-5) as flame retardants, and 0.2 part by mass of an antioxidant (manufactured by Ciba-Geigy: IRGANOX 1010) were added to and mixed with one another.

The above-mentioned mixture was molten with a side flow type biaxial extruder set at 280° C. Further, 25 parts by mass of glass fibers each having a surface treated with a silane coupling agent and each having a fiber length of about 3 mm (manufactured by ASAHI FIBERGLASS Co., Ltd.: 03.JAFT2Ak25) as reinforced fibers were mixed into the above-mentioned mixture molten from a side by means of extrusion kneading, whereby a resin pellet was obtained. After that, the above-mentioned resin pellet was dried at 105° C. for 4 hours, and was then molded with an injection molding machine (manufactured by FUNUC: α50C) under general conditions including a cylinder temperature of 280° C., a mold temperature of 80° C., an injection pressure of 78.4 MPa, an injection speed of 120 mm/s, and a cooling time of 15 seconds.

After that, the above-mentioned molded article was irradiated with γ-rays at a dose of 25 kGy by using cobalt 60 as a radiation source, whereby a resin processed article of Example 26 was obtained.

Example 27

A resin processed article of Example 27 was obtained under conditions identical to those of Example 26 except that: 46.3 parts by mass of 66 nylon (manufactured by UBE INDUSTRIES, LTD.: 2020B) were used as a thermoplastic resin; and 8 parts by mass of a reactive flame retardant represented by the above formula (I-4) and 5 parts by mass of an organophosphorus addition type flame retardant (manufactured by SANKO CHEMICAL CO., Ltd.: BCA) were used as flame retardants.

Example 28

45.2 parts by mass of 66 nylon (manufactured by UBE INDUSTRIES, LTD.: 2020B) as a thermoplastic resin, 6 parts by mass of talc having a particle diameter of 2 μm (manufactured by Nippon Talc Co., Ltd.) and 5 parts by mass of clay having a nano particle diameter (manufactured by Nissho Iwai Bentonite: NANOMER 1.30T) as inorganic fillers, 0.5 part by mass of carbon black as a colorant, 9 parts by mass of a reactive flame retardant represented by the above formula (I-1), 2 parts by mass of a multifunctional cyclic compound (manufactured by Nippon Kasei Chemical Co., LTD.: TAIC), 7 parts by mass of an organophosphorus addition type flame retardant (manufactured by SANKO CHEMICAL CO., Ltd.: BCA) as flame retardants, and 0.3 part by mass of an antioxidant (manufactured by Ciba-Geigy: IRGANOX 1010) were added to and mixed with one another.

The above-mentioned mixture was molten with a side flow type biaxial extruder set at 280° C. Further, 25 parts by mass of glass fibers each having a surface treated with a silane coupling agent and each having a fiber length of about 3 mm (manufactured by ASAHI FIBERGLASS Co., Ltd.: 03.JAFT2Ak25) as reinforced fibers were mixed into the above-mentioned mixture molten from a side by means of extrusion kneading, whereby a resin pellet was obtained. After that, the above-mentioned resin pellet was dried at 105° C. for 4 hours, and was then molded with an injection molding machine (manufactured by FUNUC: α50C) under general conditions including a cylinder temperature of 280° C., a mold temperature of 80° C., an injection pressure of 78.4 MPa, an injection speed of 120 mm/s, and a cooling time of 15 seconds.

After that, the above-mentioned molded article was irradiated with γ-rays at a dose of 25 kGy by using cobalt 60 as a radiation source, whereby a resin processed article of Example 28 was obtained.

Example 29

A molded article was molded under conditions identical to those of Example 26 except that: 48.3 parts by mass of a polybutylene terephthalate resin (manufactured by Toray Industries, Inc.: TORAYCON 1401X06) as a thermoplastic resin, 10 parts by mass of a reactive flame retardant represented by the above formula (I-1), 5 parts by mass of an organophosphorus addition type flame retardant (manufactured by SANKO CHEMICAL CO., Ltd.: BCA), and 2 parts by mass of a multifunctional cyclic compound (manufactured by TOAGOSEI CO., LTD.: M-315) as flame retardants, 10 parts by mass of talc having a particle diameter of 2 μm (manufactured by Nippon Talc Co., Ltd.) and 4 parts by mass of clay having a nano particle diameter (manufactured by Nissho Iwai Bentonite: NANOMER 1.30T) as inorganic fillers, 20 parts by mass of glass fibers each having a surface treated with a silane coupling agent and each having a fiber length of about 3 mm (manufactured by ASAHI FIBER GLASS Co., Ltd.: 03.JAFT2Ak25) as reinforced fibers, 0.5 part by mass of carbon black as a colorant, and 0.2 part by mass of an antioxidant (manufactured by Ciba-Geigy: IRGANOX 1010) were kneaded at a kneading temperature of 245° C. so that a resin pellet was obtained; the resin pellet was dried at 130° C. for 3 hours; and a cylinder temperature at the time of molding was changed to 250° C.

After that, the above-mentioned molded article was irradiated with electron beams at an irradiation dose of 40 kGy by using an accelerator manufactured by Sumitomo Heavy Industries, Ltd. at an acceleration voltage of 4.8 MeV, whereby a resin processed article of Example 29 was obtained.

Example 30

A molded article was molded under conditions identical to those of Example 26 except that 3 parts by mass of a heat catalyst (manufactured by NOF CORPORATION: Nofmer BC) were further added to the system of Example 26.

After that, the above-mentioned molded article was subjected to a reaction at 245° C. for 8 hours under heat, whereby a resin processed article of Example 30 was obtained.

Example 31

A thin molded article (having a thickness t of 0.6 mm) was molded under conditions identical to those of Example 28 except that 7 parts by mass of UV initiators (IRGANOX 651 and IRGANOX 369 manufactured by Ciba-Geigy were used in combination at a ratio of 2:1) were further added to the system of Example 28.

After that, the above-mentioned molded article was irradiated with light from an ultra-high pressure mercury lamp having a wavelength of 365 nm and an illuminance of 150 mW/cm$^2$ for 2 minutes, whereby a resin processed article of Example 31 was obtained.

Example 32

45 parts by mass of silica (Silia 530 manufactured by FUJI SILYSIA CHEMICAL LTD.) were dispersed in 45 parts by mass of a thermosetting epoxy-based mold resin obtained by mixing 100 parts by mass of a principal agent (manufactured by NAGASE CHEMICAL CO., LTD.: XNR 4012) with 50 parts by mass of a curing agent (manufactured by NAGASE CHEMICAL CO., LTD.: XNH 4012) and 1 part by mass of a curing accelerator (manufactured by NAGASE CHEMICAL CO., LTD.: FD 400), and 10 parts by mass of a reactive flame retardant represented by the above formula (I-5) were added as a flame retardant to the dispersion, whereby a molded article was obtained.

After that, the above-mentioned molded article was subjected to a reaction at 100° C. for 1 hour, whereby a resin processed article of Example 32 (sealing agent) was obtained.

Example 33

A molded article was obtained by adding 8 parts by mass of a reactive flame retardant represented by the above formula (I-5) as a flame retardant to 92 parts by mass of an epoxy resin for sealing a semiconductor (manufactured by Shin-Etsu Chemical Co., Ltd.: SEMICOAT 115).

After that, the above-mentioned molded article was subjected to a reaction at 150° C. for 4 hours, whereby a resin processed article of Example 33 (sealing agent) was obtained.

Example 34

47.3 parts by mass of a 6/66 nylon copolymer (manufactured by UBE INDUSTRIES, LTD.: 2123B) as a thermoplastic resin, 30 parts by mass of glass fibers each having a surface treated with a silane coupling agent and each having a fiber length of about 3 mm (manufactured by ASAHI FIBER GLASS Co., Ltd.: 03.JAFT2Ak25) as reinforced fibers, 0.5 part by mass of carbon black as a colorant, 0.2 part by mass of an antioxidant (manufactured by Ciba-Geigy: IRGANOX 1010), 7 parts by mass of talc having a particle diameter of 2 μm (manufactured by Nippon Talc Co., Ltd.) and 5 parts by mass of clay having a nano particle diameter (manufactured by Nissho Iwai Bentonite: NANOMER 1.30T) as inorganic fillers, and 10 parts by mass of a reactive flame retardant represented by the above formula (II-4) as a flame retardant were blended with one another, and the whole was kneaded with a side flow type biaxial extruder (manufactured by The Japan Steel Works, LTD.) at 280° C., whereby a resin pellet was obtained. After having been dried at 105° C. for 4 hours, the above-mentioned resin pellet was molded with an injection molding machine (manufactured by FUNUC: α50C) under conditions including a resin temperature of 280° C. and a mold temperature of 80° C.

After that, the above-mentioned molded article was irradiated with γ-rays at a dose of 25 kGy by using cobalt 60 as a radiation source, whereby a resin processed article of Example 34 was obtained.

Example 35

A resin processed article of Example 35 was obtained under mixing composition and molding conditions identical to those of Example 34 except that: 46.3 parts by mass of 66 nylon (manufactured by UBE INDUSTRIES, LTD.: 2020B) were used as a thermoplastic resin; 7 parts by mass of talc having a particle diameter of 2 μm (manufactured by Nippon Talc Co., Ltd.) and 4 parts by mass of clay having a nano particle diameter (manufactured by Nissho Iwai Bentonite: NANOMER 1.30T) were used as inorganic fillers; and 12 parts by mass of a reactive flame retardant represented by the above formula (I-8) were used as a flame retardant.

Example 36

42.3 parts by mass of 66 nylon (manufactured by UBE INDUSTRIES, LTD.: 2020B) as a thermoplastic resin, 11 parts by mass of silica (Silia 530 manufactured by FUJI SILYSIA CHEMICAL LTD.) and 4 parts by mass of clay having a nano particle diameter (manufactured by Nissho Iwai Bentonite: NANOMER 1.30T) as inorganic fillers, 0.5 part by mass of carbon black as a colorant, 6 parts by mass of a reactive flame retardant represented by the above formula (II-8) and 6 parts by mass of a reactive flame retardant represented by the above formula (II-9) as flame retardants, and 0.2 part by mass of an antioxidant (manufactured by Ciba-Geigy: IRGANOX 1010) were added to and mixed with one another.

The above-mentioned mixture was molten with a side flow type biaxial extruder set at 280° C. Further, 30 parts by mass of glass fibers each having a surface treated with a silane coupling agent and each having a fiber length of about 3 mm (manufactured by ASAHI FIBERGLASS Co., Ltd.: 03.JAFT2Ak25) as reinforced fibers were mixed into the above-mentioned mixture molten from a side by means of extrusion kneading, whereby a resin pellet was obtained. After that, the above-mentioned resin pellet was dried at 105° C. for 4 hours, and was then molded with an injection molding machine (manufactured by FUNUC: α50C) under general conditions including a cylinder temperature of 280° C., a mold temperature of 80° C., an injection pressure of 78.4 MPa, an injection speed of 120 mm/s, and a cooling time of 15 seconds, whereby a molded product for an electrical or electronic component or an automobile was obtained.

After that, the above-mentioned molded article was irradiated with γ-rays at an irradiation dose of 25 kGy by using cobalt 60 as a radiation source, whereby a resin processed article of Example 36 was obtained.

Example 37

A resin processed article of Example 37 was obtained under mixing composition and molding conditions identical to those of Example 36 except that: 38.3 parts by mass of 66 nylon (manufactured by UBE INDUSTRIES, LTD.: 2020B) were used as a thermoplastic resin; and 9 parts by mass of a reactive flame retardant represented by the above formula (II-8) and 7 parts by mass of an organophosphorus addition type flame retardant (manufactured by SANKO CHEMICAL CO., Ltd.: BCA) were used as flame retardants.

Example 38

A resin processed article of Example 38 was obtained under molding conditions identical to those of Example 36 except that: 44.2 parts by mass of 66 nylon (manufactured by UBE INDUSTRIES, LTD.: 2020B) were used as a thermoplastic resin; 25 parts by mass of glass fibers each having a surface treated with a silane coupling agent and each having a fiber length of about 3 mm (manufactured by ASAHI FIBERGLASS Co., Ltd.: 03.JAFT2Ak25) were used as reinforced fibers; 0.5 part by mass of carbon black was used as a colorant; 0.3 part by mass of an antioxidant (manufactured by Ciba-Geigy: IRGANOX 1010) was used; 7 parts by mass of talc having a particle diameter of 2 μm (manufactured by Nippon Talc Co., Ltd.) and 4 parts by mass of clay having a nano particle diameter (manufactured by Nissho Iwai Bentonite: NANOMER 1.30T) were used as inorganic fillers; and 10 parts by mass of a reactive flame retardant represented by the above formula (II-1), 2 parts by mass of a multifunctional cyclic compound (manufactured by Nippon Kasei Chemical Co., LTD.: TAIC), and 7 parts by mass of an organophosphorus addition type flame retardant (manufactured by Clariant: EXOLIT OP 1230) were used as flame retardants.

Example 39

51.3 parts by mass of a polybutylene terephthalate resin (manufactured by Toray Industries, Inc.: TORAYCON 1401×06) as a thermoplastic resin, 10 parts by mass of a reactive flame retardant represented by the above formula (II-12), 7 parts by mass of an organophosphorus addition type flame retardant (manufactured by SANKO CHEMICAL CO., Ltd.: BCA), and 2 parts by mass of a multifunctional cyclic compound (manufactured by TOAGOSEI CO., LTD.: M-315) as flame retardants, 5 parts by mass of talc having a particle diameter of 2 µm (manufactured by Nippon Talc Co., Ltd.) and 4 parts by mass of clay having a nano particle diameter (manufactured by Nissho Iwai Bentonite: NANOMER 1.30T) as inorganic fillers, 0.5 part by mass of carbon black as a colorant, and 0.2 part by mass of an antioxidant (manufactured by Ciba-Geigy: IRGANOX 1010) were added to and mixed with one another.

The above-mentioned mixture was molten with a side flow type biaxial extruder set at 245° C. Further, 20 parts by mass of glass fibers each having a surface treated with a silane coupling agent and each having a fiber length of about 3 mm (manufactured by ASAHI FIBERGLASS Co., Ltd.: 03.JAFT2Ak25) as reinforced fibers were mixed into the above-mentioned mixture molten from a side by means of extrusion kneading, whereby a resin pellet was obtained. After that, the above-mentioned resin pellet was dried at 130° C. for 3 hours, and was then molded with an injection molding machine (manufactured by FUNUC: α50C) under general conditions including a cylinder temperature of 250° C., a mold temperature of 80° C., an injection pressure of 78.4 MPa, an injection speed of 120 mm/s, and a cooling time of 15 seconds, whereby a molded product for an electrical or electronic component or an automobile was obtained.

After that, the above-mentioned molded article was irradiated with electron beams at an irradiation dose of 40 kGy by using an accelerator manufactured by Sumitomo Heavy Industries, Ltd. at an acceleration voltage of 4.8 MeV, whereby a resin processed article of Example 39 was obtained.

Example 40

A molded article was molded under conditions identical to those of Example 36 except that 3 parts by mass of a heat catalyst (manufactured by NOF CORPORATION: Nofmer BC) were further added to the system of Example 36.

After that, the above-mentioned molded article was subjected to a reaction at 245° C. for 8 hours under heat, whereby a resin processed article of Example 40 was obtained.

Example 41

A thin molded article (having a thickness t of 0.6 mm) was molded under conditions identical to those of Example 38 except that 7 parts by mass of UV initiators (IRGANOX 651 and IRGANOX 369 manufactured by Ciba-Geigy were used in combination at a ratio of 2:1) were further added to the system of Example 38.

After that, the above-mentioned molded article was irradiated with light from an ultra-high pressure mercury lamp having a wavelength of 365 nm and an illuminance of 150 mW/cm² for 2 minutes, whereby a resin processed article of Example 41 was obtained.

Example 42

45 parts by mass of silica (Silia 530 manufactured by FUJI SILYSIA CHEMICAL LTD.) were dispersed in 45 parts by mass of a thermosetting epoxy-based mold resin obtained by mixing 100 parts by mass of a principal agent (manufactured by NAGASE CHEMICAL CO., LTD.: XNR 4012) with 50 parts by mass of a curing agent (manufactured by NAGASE CHEMICAL CO., LTD.: XNH 4012) and 1 part by mass of a curing accelerator (manufactured by NAGASE CHEMICAL CO., LTD.: FD 400), and 10 parts by mass of a reactive flame retardant represented by the above formula (II-5) were added as a flame retardant to the dispersion, whereby a molded article was obtained.

After that, the above-mentioned molded article was subjected to a reaction at 100° C. for 1 hour, whereby a resin processed article of Example 42 (sealing agent) was obtained.

Example 43

A molded article was obtained by adding 6 parts by mass of a reactive flame retardant represented by the above formula (II-11) as a flame retardant to 94 parts by mass of an epoxy resin for sealing a semiconductor (manufactured by Shin-Etsu Chemical Co., Ltd.: SEMICOAT 115).

After that, the above-mentioned molded article was subjected to a reaction at 150° C. for 4 hours, whereby a resin processed article of Example 43 (sealing agent) was obtained.

Example 44

51.3 parts by mass of 66 nylon (manufactured by UBE INDUSTRIES, LTD.: 2020B) as a thermoplastic resin, 25 parts by mass of glass fibers each having a surface treated with a silane coupling agent and each having a fiber length of about 3 mm (manufactured by ASAHI FIBER GLASS Co., Ltd.: 03.JAFT2Ak25) as reinforced fibers, 0.5 part by mass of carbon black as a colorant, 0.2 part by mass of an antioxidant (manufactured by Ciba-Geigy: IRGANOX 1010), 6 parts by mass of talc having a particle diameter of 2 µm (manufactured by Nippon Talc Co., Ltd.) and 5 parts by mass of clay having a nano particle diameter (manufactured by Nissho Iwai Bentonite: NANOMER 1.30T) as inorganic fillers, and 12 parts by mass of a reactive flame retardant represented by the above formula (I-6) as a flame retardant were blended with one another, and the whole was kneaded with a side flow type biaxial extruder (manufactured by The Japan Steel Works, LTD.) at 280° C., whereby a resin pellet was obtained. After that, the above-mentioned resin pellet was dried at 105° C. for 4 hours, and was then molded with an injection molding machine (manufactured by FUNUC: α50C) under general conditions including a cylinder temperature of 280° C., a mold temperature of 80° C., an injection pressure of 78.4 MPa, an injection speed of 120 mm/s, and a cooling time of 15 seconds.

After that, the above-mentioned molded article was irradiated with γ-rays at a dose of 25 kGy by using cobalt 60 as a radiation source, whereby a resin processed article of Example 44 was obtained.

Example 45

A resin processed article of Example 45 was obtained under mixing composition and molding conditions identical to those of Example 44 except that 12 parts by mass of a reactive flame retardant represented by the above formula (II-17) were used as a flame retardant in Example 44.

Comparative Examples 1 to 20

Resin processed articles of Comparative Examples 1 to 20 were each obtained under mixing and molding conditions identical to those of each of Examples 24 to 43 except that the reactive flame retardant of the present invention was not blended in each of Examples 24 to 43.

Comparative Example 21

A resin processed article of Comparative Example 21 was obtained under conditions identical to those of Example 28 except that only 20 parts by mass of an organophosphorus addition type flame retardant (manufactured by SANKO CHEMICAL CO., Ltd.: BCA) were added as a flame retardant in Example 28.

Comparative Example 22

A resin processed article of Comparative Example 22 was obtained under conditions identical to those of Example 38 except that only 20 parts by mass of an organophosphorus addition type flame retardant (manufactured by SANKO CHEMICAL CO., Ltd.: BCA) were added as a flame retardant in Example 38.

Comparative Example 23

A resin processed article of Comparative Example 23 was obtained under mixing composition and molding conditions identical to those of Example 44 except that 12 parts by mass of a reactive flame retardant represented by the following formula (III-1) were used as a flame retardant in Example 44.

[Chem 23]

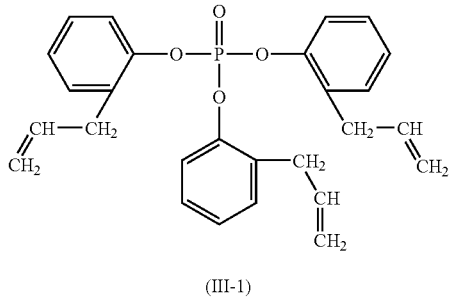

(III-1)

(Physical Property Test for Flame-retardant Resin Processed Article)

Test Example 2

For each of the resin processed articles of Examples 24 to 43 and Comparative Examples 1 to 22, a test piece (measuring 5 inches long by ½ inch wide by 3.2 mm thick) in conformance with UL-94 as a flame retardance test and a glow-wire test piece (60 mm square, having a thickness of 1.6 mm) in conformance with an IEC60695-2 method (GWFI) were created, and the test pieces were subjected to a UL 94 test, a glow-wire test (in conformance with IEC), and a solder heat resistance test. In addition, all the resin processed articles were subjected to a bleed out test at 300° C. for 3 hours. Tables 2 and 3 collectively show the results.

In the UL 94 test, a test piece was vertically mounted and in contact with the flame of a Bunsen burner for 10 seconds to record a burning time. After being extinguished, the test piece was in contact with the flame for 10 seconds again to record a burning time. A total of burning times, a glowing time after the second extinguishment, and the presence or absence of a dropped product for igniting cotton were determined.

In addition, the glow-wire test was performed by using a nichrome wire of 4 mm in diameter (composed of 80% of nickel and 20% of chromium) as a glow-wire that is bent to prevent tip thereof from splitting and by using a type K (Chromel-Alumel) of 0.5 mm in diameter as a thermocouple for measurement of temperature under a thermocouple pressing load of 1.0±0.2 N and a temperature of 850° C. The criterion in which the burning time after contact is less than 30 seconds and in which tissue paper below a sample fails to ignite was used as determination of combustibility (GWFI).

In the solder heat resistance test, a rate of change in dimensions after immersion in a bath of molten solder at 350° C. for seconds was shown.

TABLE 2

| | Flame retardancy (UL-94) | Kindler to reach clamp | Ignition of absorbent cotton due to dropped product | Glow-wire test | Bleed out after 3 hours at 300° C. | Rate of change in dimensions in solder heat resistance test (%) |
|---|---|---|---|---|---|---|
| Example 24 | V-0 | Absent | Absent | Passed | Absent | 4 |
| Example 25 | V-0 | Absent | Absent | Passed | Absent | 3 |
| Example 26 | V-0 | Absent | Absent | Passed | Absent | 3 |
| Example 27 | V-0 | Absent | Absent | Passed | Absent | 5 |
| Example 28 | V-0 | Absent | Absent | Passed | Absent | 5 |
| Example 29 | V-0 | Absent | Absent | Passed | Absent | 6 |
| Example 30 | V-0 | Absent | Absent | Passed | Absent | 11 |
| Example 31 | V-0 | Absent | Absent | Passed | Absent | 18 |
| Example 32 | V-0 | Absent | Absent | Passed | Absent | 5 |
| Example 33 | V-0 | Absent | Absent | Passed | Absent | 27 |
| Example 34 | V-0 | Absent | Absent | Passed | Absent | 3 |
| Example 35 | V-0 | Absent | Absent | Passed | Absent | 3 |
| Example 36 | V-0 | Absent | Absent | Passed | Absent | 3 |
| Example 37 | V-0 | Absent | Absent | Passed | Absent | 6 |
| Example 38 | V-0 | Absent | Absent | Passed | Absent | 6 |

TABLE 2-continued

| | Flame retardancy (UL-94) | Kindler to reach clamp | Ignition of absorbent cotton due to dropped product | Glow-wire test | Bleed out after 3 hours at 300° C. | Rate of change in dimensions in solder heat resistance test (%) |
|---|---|---|---|---|---|---|
| Example 39 | V-0 | Absent | Absent | Passed | Absent | 7 |
| Example 40 | V-0 | Absent | Absent | Passed | Absent | 11 |
| Example 41 | V-0 | Absent | Absent | Passed | Absent | 15 |
| Example 42 | V-0 | Absent | Absent | Passed | Absent | 19 |
| Example 43 | V-0 | Absent | Absent | Passed | Absent | 25 |

TABLE 3

| Comparative examples | Flame retardancy (UL-94) | Kindler to reach clamp | Ignition of absorbent cotton due to dropped product | Glow-wire test | Bleed out after 3 hours at 300° C. | Rate of change in dimensions in solder heat resistance test (%) |
|---|---|---|---|---|---|---|
| 1 | HB | Present | Present | Failed | Absent | Deformed* |
| 2 | HB | Present | Present | Failed | Absent | Deformed* |
| 3 | HB | Present | Present | Failed | Absent | Deformed* |
| 4 | HB | Present | Present | Failed | Absent | 29 |
| 5 | HB | Present | Present | Failed | Absent | 33 |
| 6 | HB | Present | Present | Failed | Absent | Deformed* |
| 7 | HB | Present | Present | Failed | Absent | Deformed* |
| 8 | HB | Present | Present | Failed | Absent | Deformed* |
| 9 | HB | Present | Present | Failed | Absent | Deformed* |
| 10 | HB | Present | Present | Failed | Absent | Deformed* |
| 11 | HB | Present | Present | Failed | Absent | Deformed* |
| 12 | HB | Present | Present | Failed | Absent | Deformed* |
| 13 | HB | Present | Present | Failed | Absent | Deformed* |
| 14 | HB | Present | Present | Failed | Absent | 28 |
| 15 | HB | Present | Present | Failed | Absent | 32 |
| 16 | HB | Present | Present | Failed | Absent | Deformed* |
| 17 | HB | Present | Present | Failed | Absent | Deformed* |
| 18 | HB | Present | Present | Failed | Absent | Deformed* |
| 19 | HB | Present | Present | Failed | Absent | Deformed* |
| 20 | HB | Present | Present | Failed | Absent | Deformed* |
| 22 | V-2 | Absent | Present | Passed | Present | Deformed* |
| 23 | V-2 | Absent | Present | Passed | Present | Deformed* |

Deformed* Deformed immediately after immersion

As can be seen from the results shown in Tables 2 and 3, each of all the resin processed articles of Examples had flame retardance of V-0 (that is, each resin processed article was excellent in flame retardance) and passed the glow-wire test. Further, in each of all the resin processed articles of Examples, a rate of change in dimensions after the solder heat resistance test was 27% or less. In addition, a flame retardant was not observed to bleed out even after 3 hours at 300° C.

On the other hand, each of all the resin processed articles of Comparative Examples 1 to 20 not containing any reactive flame retardant of the present invention had flame retardance of HB (that is, insufficient flame retardance) and failed the glow-wire test. Further, regarding the rate of change in dimensions after the solder heat resistance test, that was worsen as compared to respective Examples.

In addition, the resin processed article of Comparative Examples 21 and 22 using a non-reactive organophosphorus-based flame retardant as a flame retardant had flame retardance of V-2 (that is, insufficient flame retardance), and was observed to bleed out after 3 hours at 300° C.

Test Example 3

The storage modulus of each of the resin processed articles of Example 44, Example 45, and Comparative Example 23 was measured with a PHYSICA UDS 200 (manufactured by Nihon SiberHegner) under conditions including a temperature range of 45 to 350° C., a rate of temperature increase of 5° C./min, a driving frequency of 1 Hz, and an applied distortion of 0.2%. FIG. 2 shows the results.

The results of FIG. 2 show that Examples 44 and 45 each using the organophosphorus compound of the present invention were each excellent in mechanical strength.

On the other hand, the resin processed article of Comparative Example 23 was inferior to the Examples in mechanical strength.

INDUSTRIAL APPLICABILITY

The present invention can be suitably used for resin molded articles such as an electrical component and an electronic component, as a flame-retardant resin processed article each containing no halogen.

The invention claimed is:

1. A reactive flame retardant, comprising an organophosphorus compound represented by the following general formula (I) or (II), the organophosphorus compound having a terminal unsaturated group:

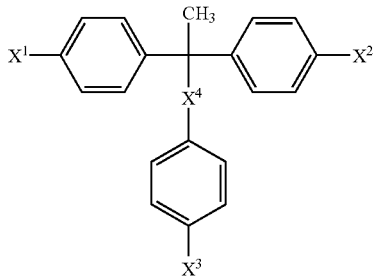
(I)

where $X^1$ to $X^3$ each independently represent —OH or a group represented by the following formula (A), $X^4$ represents a single bond or a group represented by the following formula (B), and one or more of $X^1$ to $X^3$ each represent a group represented by the following formula (A) and containing $CH_2\!=\!CH\!-\!CH_2\!-\!$ at a terminal of the group;

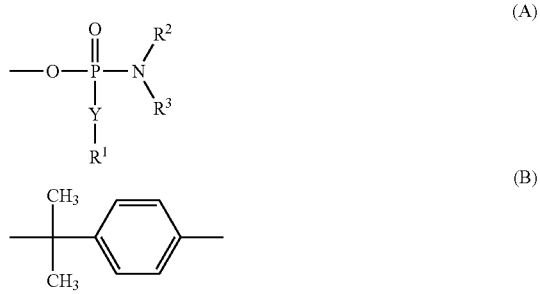
(A)

(B)

where $R^1$ represents $CH_2\!=\!CH\!-\!CH_2\!-\!$, an aryl group having 12 or less carbon atoms, or an aralkyl group having 12 or less carbon atoms, $R^2$ and $R^3$ each independently represent a hydrogen atom, $CH_2\!=\!CH\!-\!CH_2\!-\!$, an aryl group having 12 or less carbon atoms, or an aralkyl group having 12 or less carbon atoms, and Y represents a single bond, —NH—, or —O—;

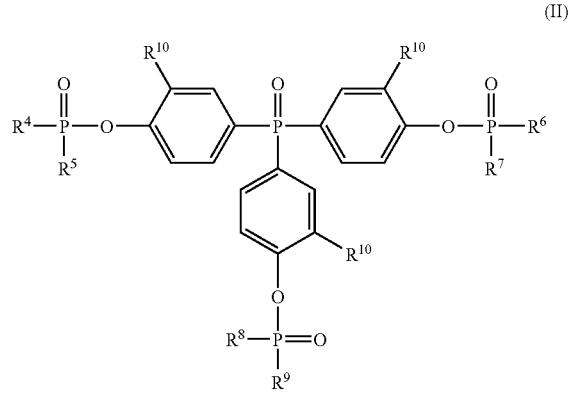
(II)

where $R^4$ to $R^9$ each represent a group selected from phenyl, benzyl, α-naphthyl, β-naphthyl, p-biphenyl, phenoxy, benzyloxy, α-naphthoxy, β-naphthoxy, p-biphenyloxy, $(CH_2\!=\!CH\!-\!CH_2)_2N\!-\!$, $CH_2\!=\!CH\!-\!CH_2NH\!-\!$, $CH_2\!=\!CH\!-\!CH_2O\!-\!$, and $CH_2\!=\!CH\!-\!CH_2\!-\!$ groups, $R^{10}$ represents H or $CH_2\!=\!CH\!-\!CH_2\!-\!$, at least one of $R^4$ to $R^{10}$ represents a group containing $CH_2\!=\!CH\!-\!CH_2\!-\!$, at a terminal of the group, and $R^4$ to $R^9$ may be identical to or different from one another.

2. A flame-retardant resin processed article obtained by molding or film-coating a resin composition which contains the reactive flame retardant according to claim 1 and a resin and then reacting the resin with the reactive flame retardant by heating or irradiation with a radiation, the flame-retardant resin processed article comprising 1 to 20 mass % of the reactive flame retardant with respect to an entirety of the flame-retardant resin processed article.

3. The flame-retardant resin processed article according to claim 2, wherein the resin composition contains two or more kinds of the reactive flame retardants at least one kind of which is multifunctional.

4. The flame-retardant resin processed article according to claim 2, wherein the resin composition further contains, other than the reactive flame retardant, a flame retardant being a cyclic nitrogen-containing compound having at least one unsaturated group at a terminal of the compound.

5. The flame-retardant resin processed article according to claim 2, wherein the resin composition further contains an addition type flame retardant having no reactivity.

6. The flame-retardant resin processed article according to claim 2, wherein the resin composition further contains a crosslinking agent which is a multifunctional monomer or oligomer having an unsaturated group at an end of main skeleton thereof.

7. The flame-retardant resin processed article according to claim 2, further comprising 1 to 45 mass % of an inorganic filler with respect to the entirety of the flame-retardant resin processed article.

8. The flame-retardant resin processed article according to claim 7, further comprising 1 to 10 mass % of a laminar clay obtained by laminating silicate layers as the inorganic filler with respect to the entirety of the flame-retardant resin processed article.

9. The flame-retardant resin processed article according to claim 2, further comprising 5 to 50 mass % of reinforced fibers with respect to the entirety of the flame-retardant resin processed article.

10. The flame-retardant resin processed article according to claim 2, which is obtained by a reaction between the resin and the reactive flame retardant through irradiation with an electron beam or a γ ray at a dose of 10 kGy or more.

11. The flame-retardant resin processed article according to claim 2, which is obtained by a reaction between the resin and the reactive flame retardant at a temperature higher than a temperature at which the resin composition is molded by 5° C. or higher.

12. The flame-retardant resin processed article according to claim 2, which comprises one selected from a molded article, a coating film, and a sealing compound.

13. The flame-retardant resin processed article according to claim 2, which is used as an electrical component or an electronic component.

* * * * *